US012787957B2

(12) United States Patent
Borrowman et al.

(10) Patent No.: US 12,787,957 B2
(45) Date of Patent: Nov. 10, 2026

(54) DEVICE AND METHOD FOR POLLEN APPLICATION

(71) Applicant: Monsanto Technology LLC, St. Louis, MO (US)

(72) Inventors: Eric Lee Borrowman, Saint Peters, MO (US); Zachary Boyer, Fenton, MO (US); Amanuel Ghebretinsae, Chesterfield, MO (US); Jeffrey Lawrence Kohne, Kirkwood, MO (US); Jeffrey Steven Morris, Saint Charles, MO (US); Payman Rassoolkhani, Maryland Heights, MO (US); Gretchen E. Spiess, O'Fallon, MO (US); Chad A. Stendal, O'Fallon, MO (US)

(73) Assignee: MONSANTO TECHNOLOGY LLC, Saint Louis, MO (US)

( * ) Notice: Subject to any disclaimer, the term of this patent is extended or adjusted under 35 U.S.C. 154(b) by 455 days.

(21) Appl. No.: 17/410,997

(22) Filed: Aug. 24, 2021

(65) Prior Publication Data

US 2022/0061243 A1 Mar. 3, 2022

Related U.S. Application Data

(60) Provisional application No. 63/154,395, filed on Feb. 26, 2021, provisional application No. 63/070,234, filed on Aug. 25, 2020.

(51) Int. Cl.
*A01H 1/02* (2006.01)

(52) U.S. Cl.
CPC .................................... *A01H 1/027* (2021.01)

(58) Field of Classification Search
CPC .................................................... A01G 7/06
USPC ........................................................ 47/1.41
See application file for complete search history.

(56) References Cited

U.S. PATENT DOCUMENTS

| | | | | | |
|---|---|---|---|---|---|
| 2,685,149 | A * | 8/1954 | Hvistendahl | A01H 1/027 47/1.41 |
| 3,396,008 | A | 8/1968 | Woods et al. | |
| 3,728,817 | A * | 4/1973 | Huey | A01M 21/043 47/1.41 |
| 3,943,660 | A * | 3/1976 | Hosaka | A01H 1/027 47/1.41 |
| 9,433,161 | B2 | 9/2016 | Cope et al. | |
| 2013/0118067 | A1 | 5/2013 | Cope et al. | |
| 2019/0364753 | A1 | 12/2019 | Aguiar et al. | |
| 2020/0120886 | A1* | 4/2020 | Geltner | A01G 7/06 |
| 2021/0289729 | A1* | 9/2021 | Wang | A01H 1/027 |
| 2021/0298253 | A1* | 9/2021 | Bradley | A01H 1/027 |

FOREIGN PATENT DOCUMENTS

| | | | | |
|---|---|---|---|---|
| CN | 107094614 A | 8/2017 | |
| CN | 109496835 A * | 3/2019 | A01H 1/02 |
| FR | 2979798 A1 | 3/2013 | |
| KR | 20040037515 A * | 5/2004 | |
| KR | 20090081363 A * | 7/2009 | |
| KR | 20100035503 A | 4/2010 | |

(Continued)

*Primary Examiner* — Peter M Poon
*Assistant Examiner* — Shada Mohamed Alghailani
(74) *Attorney, Agent, or Firm* — Harness, Dickey & Pierce, P.L.C.

(57) ABSTRACT

A device and method for applying pollen to crop plants.

9 Claims, 21 Drawing Sheets

(56) References Cited

FOREIGN PATENT DOCUMENTS

| | | | | | |
|---|---|---|---|---|---|
| KR | 20120106446 | A | | 9/2012 | |
| KR | 20180007106 | A | * | 1/2018 | |
| WO | WO-2018129302 | A1 | * | 7/2018 | ............. A01H 1/025 |
| WO | WO-2019241419 | A1 | | 12/2019 | |

* cited by examiner

DEVICE AND METHOD FOR POLLEN APPLICATION

CROSS-REFERENCE TO RELATED APPLICATIONS

This application claims priority to U.S. Provisional Patent Application Ser. No. 63/070,234, filed Aug. 25, 2020, and U.S. Provisional Patent Application Ser. No. 63/154,395, filed Feb. 26, 2021, which are hereby incorporated by reference in their entirety.

FIELD

The present disclosure relates to a device and method for applying pollen to crop plants, and more specifically to a device mountable on a tractor for traveling along rows of crop plants to apply pollen to the plants and related methods. p

BACKGROUND

Modern agriculture often uses pollination processes where the pollen from one group of pollen bearing crop plant grown in one field or row within a field is used to pollinate crops of another group of the pollen receiving plants grown in a separate field or row in the field. Ideally, the pollen bearing plants producing the most viable pollen are used for the pollination process. Thus, the likelihood that the pollenated plants will produce a desirable seed crop is increased. The pollen for the pollination process can be collected from the pollen bearing plants in a number of way. For instance, the pollen can be hand collected or a machine or apparatus can be used to collect the pollen from the crops. The collected pollen may also be stored for a period of time prior to being applied to the pollen receiving plants. In some cases, the pollen can be stored for up to a year before being applied to the pollen receiving plants. The present disclosure provides a pollen applicator and application process which yields a high percentage of viable seeds from pollen that has been previously collected and stored.

SUMMARY

In one aspect, a pollen applicator device for applying pollen to crop plants grown in rows generally comprises a housing assembly configured to be mounted on a base for being transported through a row of crop plants. The housing assembly is configured to receive pollen and mix the pollen as the housing assembly is transported through the row of crop plants. An applicator is attached to the housing assembly for applying the pollen to the plants as the housing assembly is transported through the row of crop plants.

In another aspect, a method of applying pollen to crop plants grown in rows generally comprises transporting a pollen applicator device along a row of crop plants. Mixing pollen in the pollen applicator device as the pollen applicator device is transported along the row of crop plants. Applying the mixed pollen to the row of crop plants as the pollen applicator device is transported along the row of crop plants.

BRIEF DESCRIPTION THE DRAWINGS

Corresponding reference characters indicate corresponding parts throughout the drawings.

DETAILED DESCRIPTION

Figure 1:
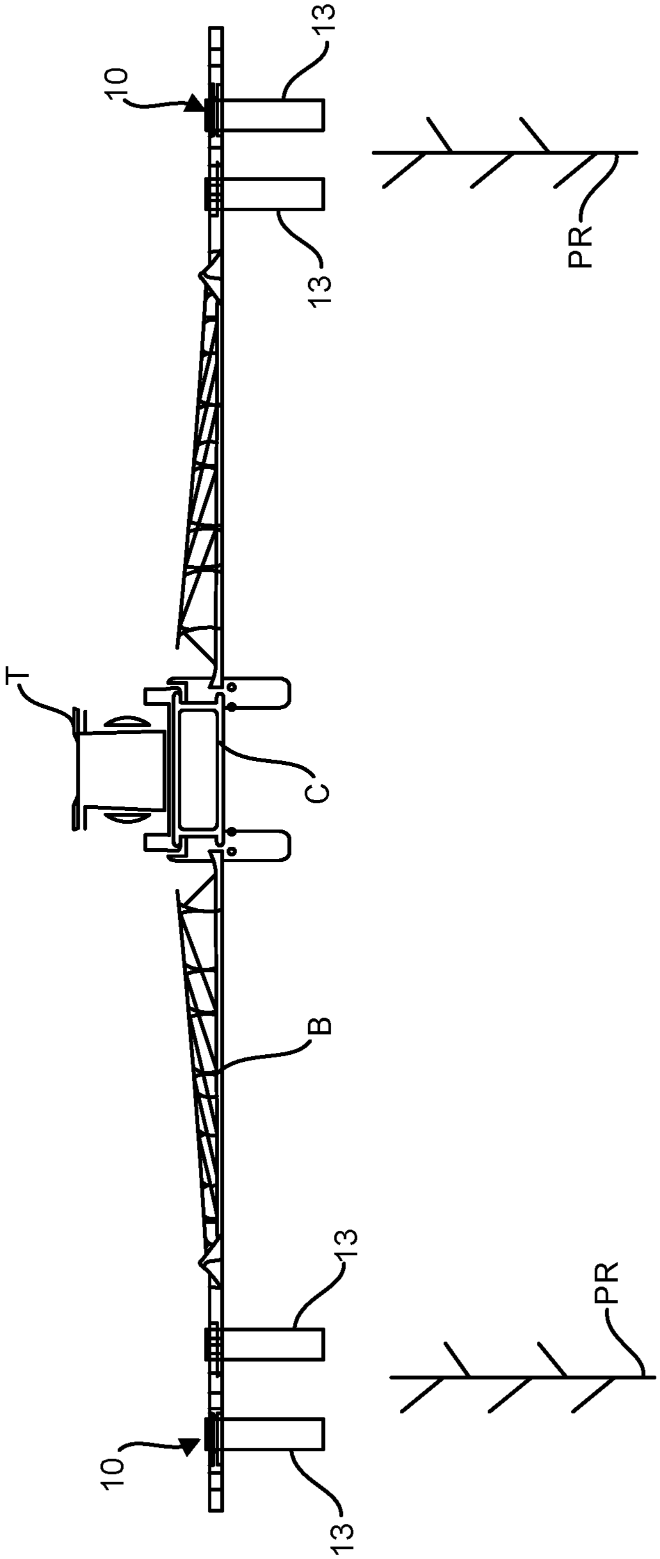
FIG. 1 is an illustration of a tractor equipped with a plurality of pollen applicator devices.
Figure 2:
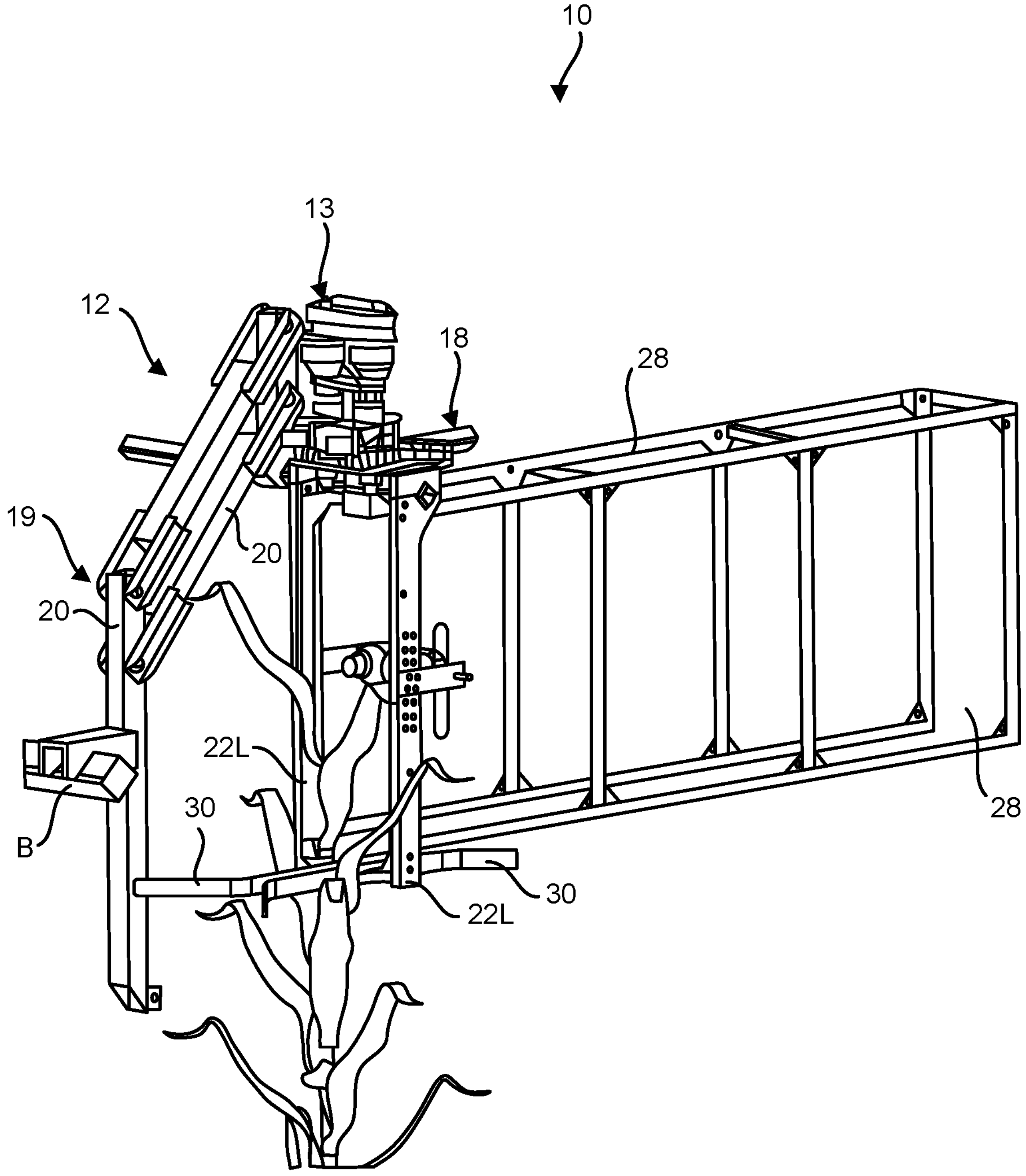
FIG. 2 is a perspective of a pollen applicator device.
Figure 3:
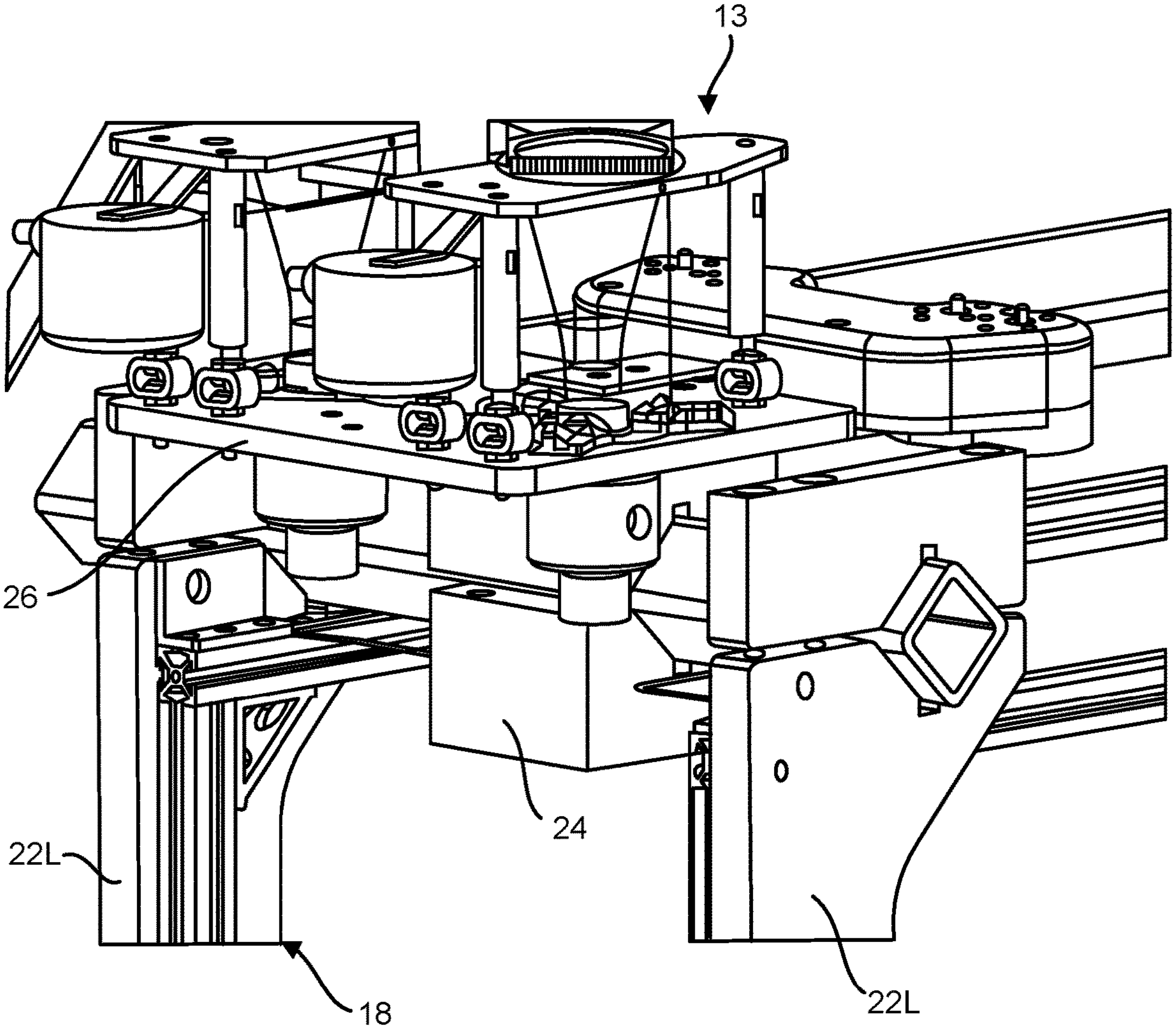
FIG. 3 is an enlarged fragmentary perspective of the pollen applicator device of FIG. 2.
Figure 4:
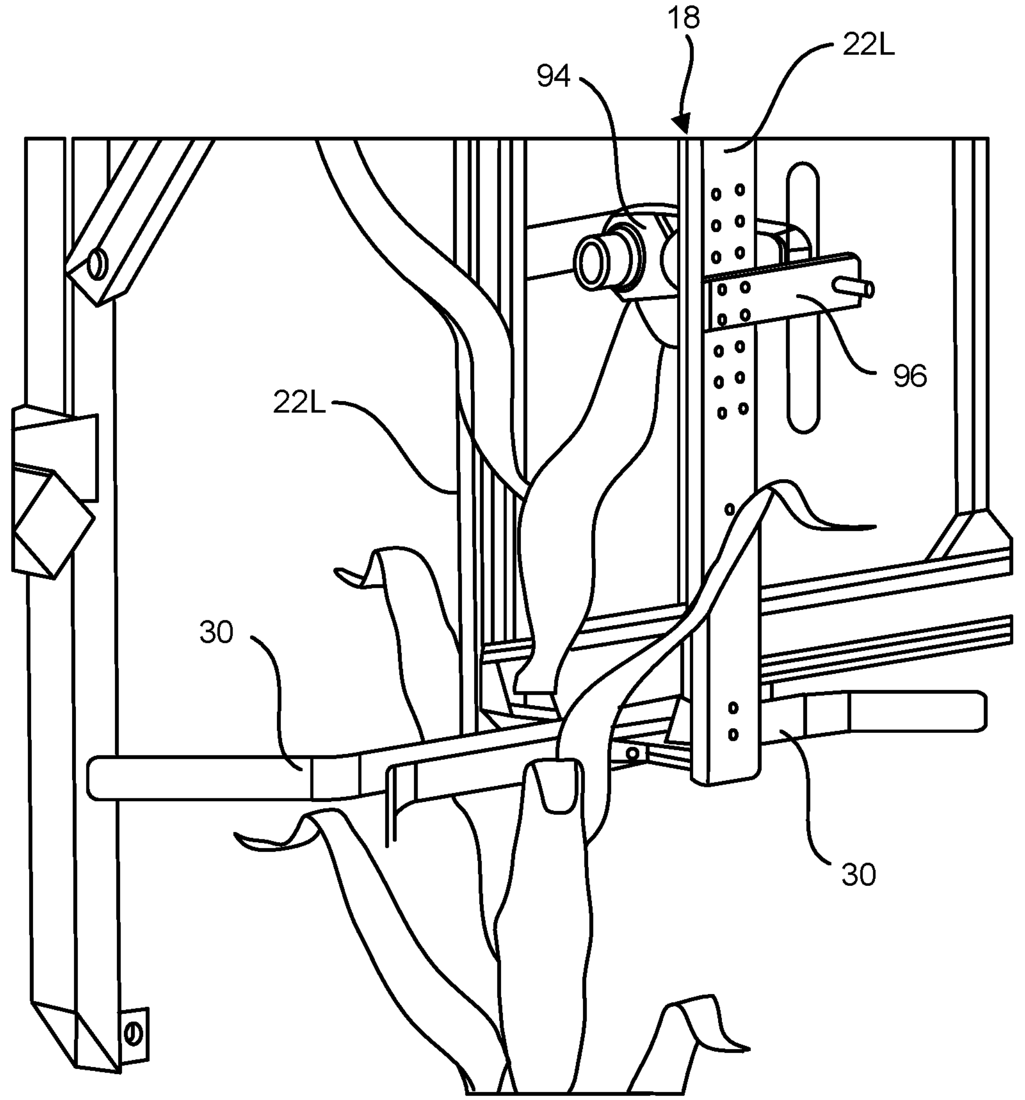
FIG. 4 is an enlarged fragmentary perspective of the pollen applicator device of FIG. 2.
Figure 5:
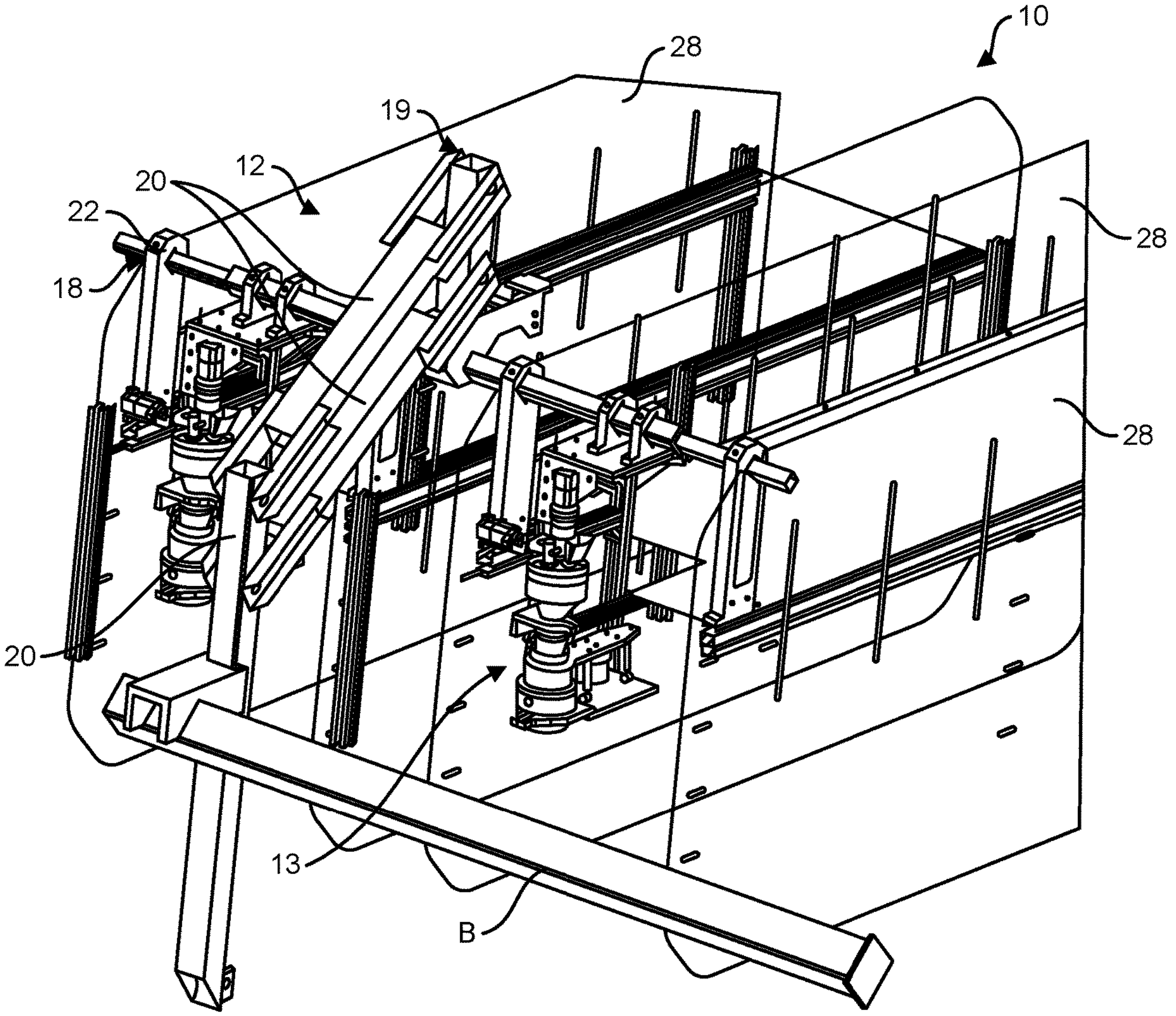
FIG. 5 is another perspective of the pollen applicator device.

Referring to FIG. 1, a tractor T may be configured to carry one or more pollen applicator devices, generally indicated at 10, for applying pollen to crops plants in a field. In one embodiment, the pollen applicator device 10 is configured to apply pollen collected from corn plants. However, it is understood that in other embodiments, a pollen applicator device can be configured to apply pollen collected from other crop plants such as, for example, canola; tomato; eggplant; sweet and hot peppers; wheat; amaranth; barley; oat; rye; wild rice; walnut; pecan; brassica such as cabbage, broccoli, spinach; and various types of trees. The tractor T may be positioned in a field to drive along the rows of crop plants while supporting the pollen applicator devices 10. The tractor T has a forward end and a rearward end and typically travels along the rows of plants in a forward direction. In the illustrated embodiment, the pollen applicator devices 10 are mounted adjacent the forward end.

Each pollen applicator device 10 is configured to be moved through a row of plants PR to apply pollen held in the device to the plants. In one embodiment, the plants PR are emasculated plants (e.g., corn plants) whereby the male parts, including the stamen(s), are removed so that they do not produce any pollen. The emasculated plants may be referred to as pollen-receiving plants because they must receive the pollen from other corn plants in order to be pollinated.

The tractor T comprises a carriage C configured to be driven along the rows of crop plants. A base B is attached to the carriage C. The base B has a width that is oriented transverse (e.g., generally perpendicular) to the forward direction of travel of the tractor T so that the base extends laterally outward from the tractor. The pollen applicator devices 10 are mounted on the base B at spaced apart locations along the width of the base. Suitably, the pollen applicator devices 10 are spaced apart along the width of the base B at intervals that correspond with the spacing of the rows of crop plants in the field so that at least one pollen applicator device 10 is disposed adjacent one of the pollen-receiving rows of plants PR as the tractor T travels through the field. In the illustrated embodiment, each applicator device 10 comprises a pair of pollen applicator assemblies 13. Each pair of pollen applicator assemblies 13 are arranged on the base B such that they are disposed on opposite sides of a row of crop plants. The tractor T may be driven at any suitable speeds for applying pollen from the plants. In one embodiment, the tractor T travels at speeds from about 2 to about 5 mph during pollen application. In one embodiment, the tractor T travels at a speed of about 3 mph. It will be understood that the tractor may travel at other speeds, such as speeds faster that 5 mph, without departing from the scope of the disclosure.

In the illustrated embodiment, the base B comprises a folding farm implement boom. The boom B is shown in the unfolded or expanded configuration. As is known in the art, a folding boom can also be folded to a compact or folded configuration (not shown) in which the width of the base is narrow enough for the tractor T to drive on a road while supporting the pollen applicator devices 10. In the illustrated embodiment, the tractor T comprises a high clearance farm tractor such as an applicator sold by Hagie Manufacturing Company of Clairon, Iowa. Other kinds of tractors or other kinds of vehicles or machines suitable for carrying the pollen applicator devices 10 through a field may be used in other embodiments. For example, manned or unmanned aerial vehicles (e.g., drones), unmanned robots, etc., can be used to carry the pollen applicator devices 10 in other embodiments. Although the illustrated embodiment shows two pollen applicator devices 10, in other embodiments the base B can have any number of pollen applicator devices 10 mounted thereon, including a single pollen applicator device. In this embodiment, the single applicator device may include multiple distribution channels for distributing the pollen to multiple rows of plants. Additionally, the pollen applicator devices 10 can be mounted to the base B in other locations and at other spacing as needed for positioning along the rows of plants.

Referring to FIGS. 2-5, each pollen applicator device 10 comprises a mounting assembly 12 configured to attach the applicator device to a support (i.e., tractor T) and a pair of applicator assemblies 13 supported by the mounting assembly for applying the pollen to the plants PR. Each applicator assembly 13 includes a housing assembly 14 (FIG. 6) secured to the mounting assembly 12 and configured to receive pollen previously collected from pollen bearing plants, and an applicator 16 (FIG. 11) connected to the housing assembly for receiving the pollen from the housing assembly and applying the pollen to the pollen receiving plants PR in a field. As will be explained in greater detail below, the housing assembly 14 is configured to deliver a specific and adjustable dose of pollen to the applicator 16 for controlling the amount of pollen applied to the plants PR as the applicator device 10 is traversed along the plants. Each application unit can be individually adjusted in order to optimize pollen dosing amounts per row thereby, minimize pollen usage and improve productivity. Moreover, the housing assembly 14 and applicator 16 are configured to handle and apply freshly collected pollen, stored pollen, and pollen mixed with additives without complications. Thus, the applicator device 10 has universal applicability in pollen application processes. Further, the pollen applicator device 10 may include one applicator assembly 13 or more than two applicator assemblies without departing from the scope of the disclosure.

The mounting assembly 12 may be used to mount the pollen applicator device 10 to the base B on the tractor T. However, the applicator device 10 may be supported on the tractor T in other ways without departing from the scope of the disclosure. Accordingly, the pollen applicator device 10 allows for continuous application of pollen as the device is moved along a row of crop plants. Therefore, the pollen applicator device 10 facilitates efficient and controllable application of pollen directly to the plant in the field.

Figure 6:
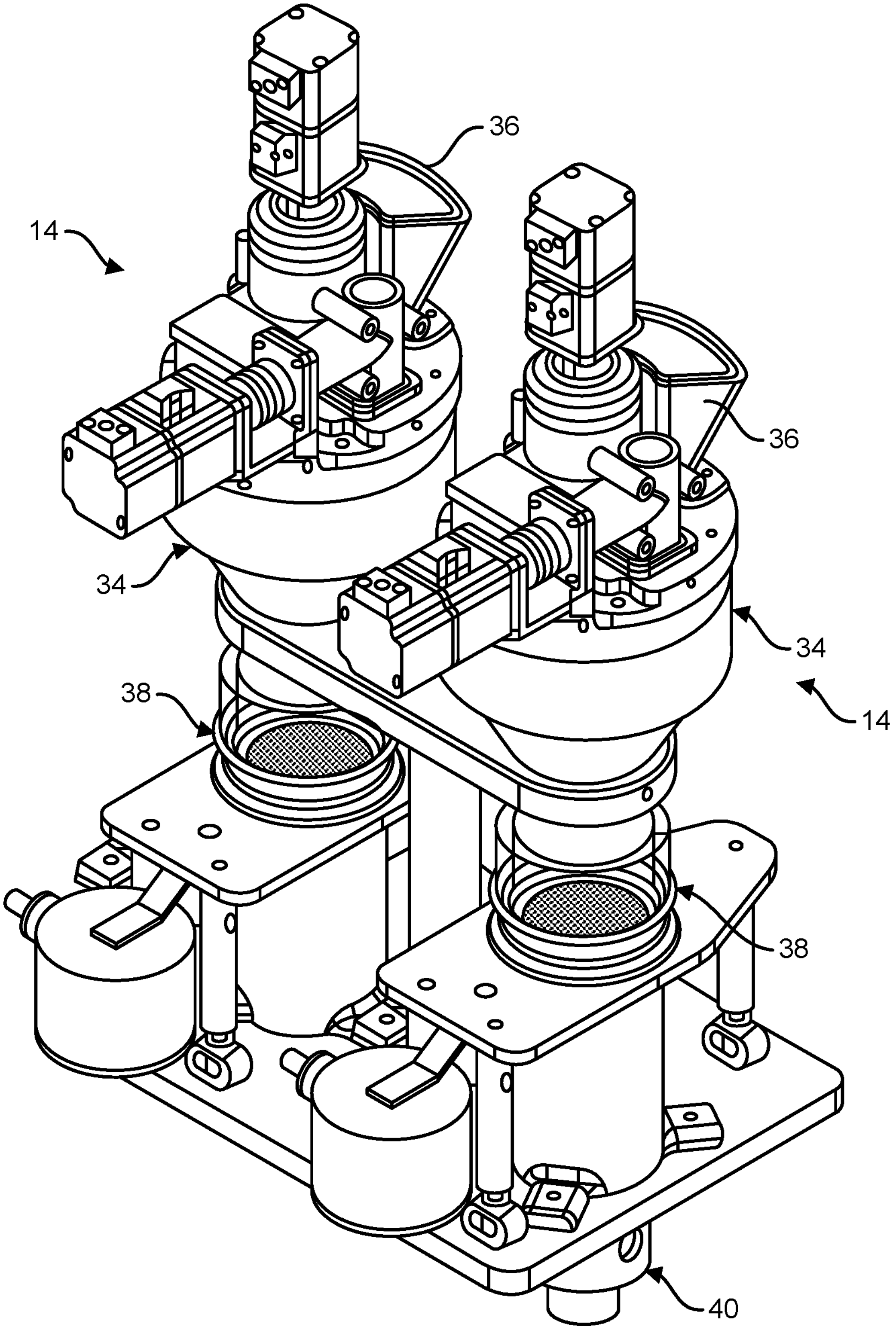
FIG. 6 is a perspective of housing assemblies of the pollen applicator device.

Referring to FIGS. 2-5, the mounting assembly 12 comprises a frame 18 for supporting the applicator assemblies 13 in a suspended position adjacent the plants PR and a linkage 19 connecting the frame to the base B of the tractor T. Brackets may be used to clamp around a portion of the base B on the tractor T for mounting the linkage 19 to the tractor. However, other means for attaching the pollen applicator device 10 to the tractor T are envisioned within the scope of the disclosure. The linkage 19 includes a plurality of link members 20 connected together for movably attaching the frame 18 to the base B of the tractor T. Thus, a position (e.g., height) of applicator assemblies 13 can adjusted by moving the linkage 19 relative to the base B. The frame 18 includes a plurality of brackets 22 providing the structure of the frame and attaching the frame to the linkage 19. The brackets 22 may be fastened to a link member 20 of the linkage 19 using fasteners (not shown). A holder 24 (FIG. 3) is attached to a center bracket 22C and supports a base plate 26 that supports the housing assemblies 14 (FIG. 6). It will be understood that the housing assemblies 14 may be supported by the mounting assembly in other ways without departing from the scope of the disclosure.

Lateral brackets 22L extend below the center bracket 22C and attach shields 28 that extend rearwardly from the lateral brackets. As will be explained in greater detail below, the shields 28 are positioned to be disposed on opposite sides of a row of crop plants and above the row of crop plants. The shields 28 are configured to contain the pollen expelled from the applicator assemblies 13 as the applicator device 10 is moved along a row of crop plants so that the pollen is directed to the row of plants and prevented from dispersing away from the plants. Thus, the shields 28 increase the chances of fertilization. Lower guides 30 are attached to the bottom of the lateral brackets 22L and extend forwardly from the brackets. The lower guides 30 flare outward as they extend from the brackets 22L to define a funnel for directing the bottom of the plants PR into the area of the pollen applicator assemblies 13. Upper guides (not shown) are attached to an intermediate location on the lateral brackets 22L and extend forwardly from the brackets. The upper guides may flare outward as they extend from the brackets 22L to define a funnel for directing the tops of the plants P into the area of the pollen applicator assemblies 13. The guides 30 may have other configurations of may be omitted without departing from the scope of the disclosure.

Figure 7:
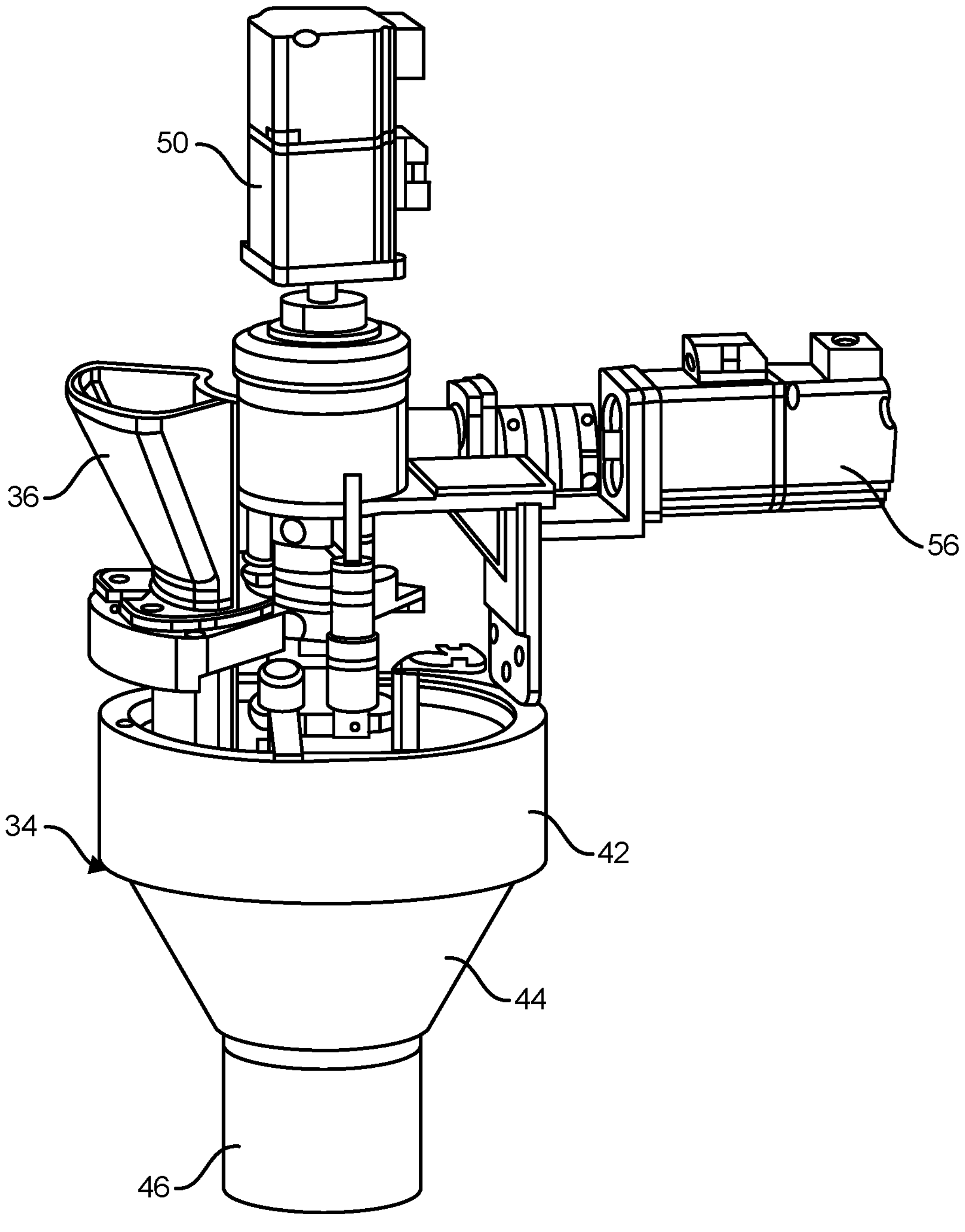
FIG. 7 is a perspective of a housing assembly of the pollen applicator device with portions removed to show internal detail.

Referring to FIGS. 6 and 7, each housing assembly 14 comprises a mixing chamber 34 for mixing the pollen in the housing assembly, a funnel 36 attached to a top of the mixing chamber for funneling the collected pollen into the mixing chamber, a sieve chamber 38 attached to the bottom of the mixing chamber for further separating and dispersing the mixed pollen, and an air flow chamber 40 attached to the bottom of the sieve chamber for directing the mixed and separated pollen out of the housing assembly. The housing assembly 14 is configured to sufficiently mix and separate the pollen such that collected pollen which may have clumped together over a period of time is able to be loosened and broken up. Therefore, pollen that is sent to the applicator 16 for being applied to the plants is in a suitable condition for fertilizing the plants. This allows pollen which may have been stored for a considerable amount of time or pollen that has been mixed with additives to be usable within the applicator device 10. It will be understood that the housing assembles 14 may have other configurations without departing from the scope of the disclosure. For instance, one or more of the chambers can be removed. In one embodiment, the air flow chamber 40 is removed such that the housing assembly uses gravity to deliver the mixed pollen to the applicator 16. Still other configurations of the housing assembly 14 are envisioned.

Figure 8:
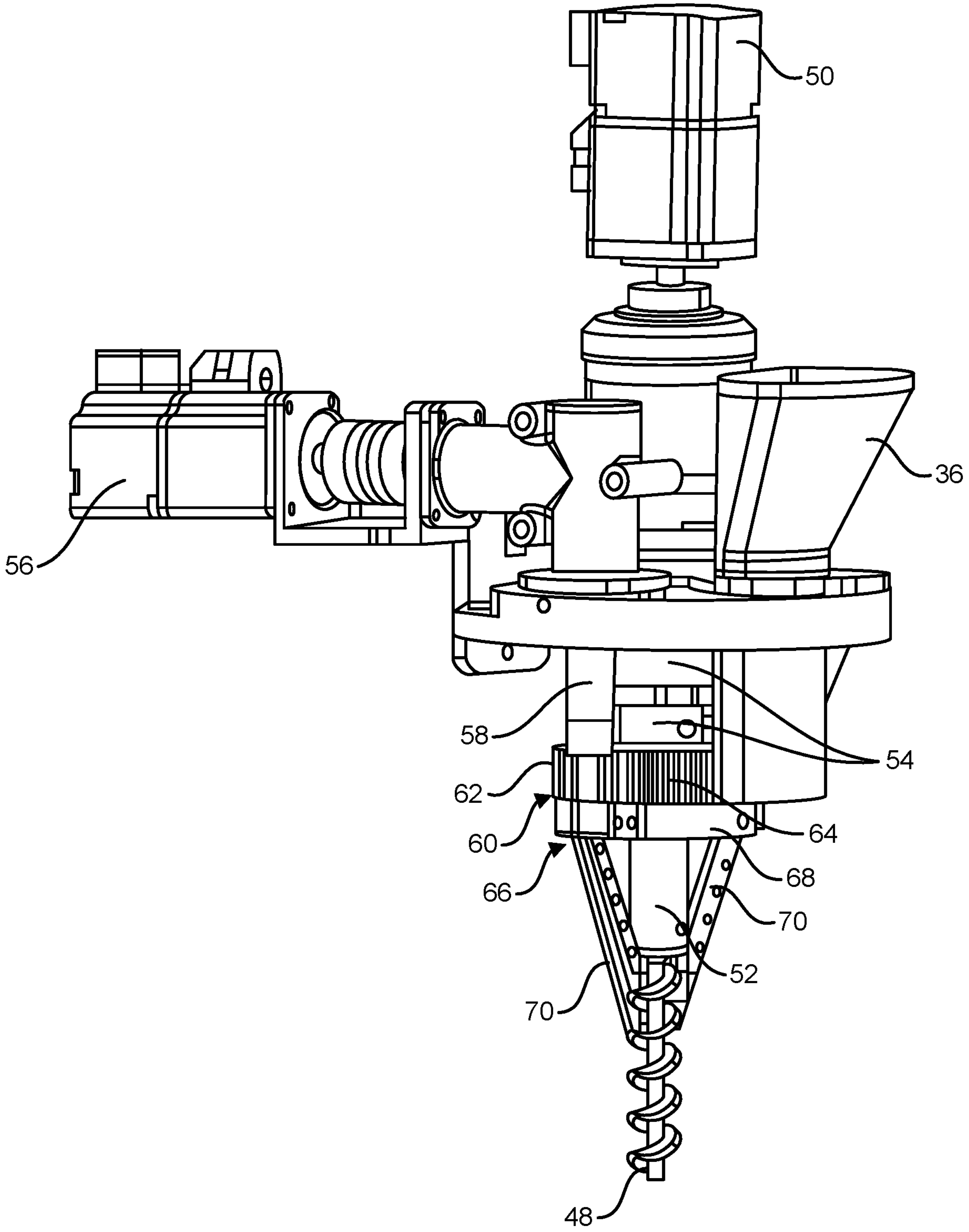
FIG. 8 is a perspective of the housing assembly of FIG. 7 with additional portions removed to show internal detail.
Figure 9:
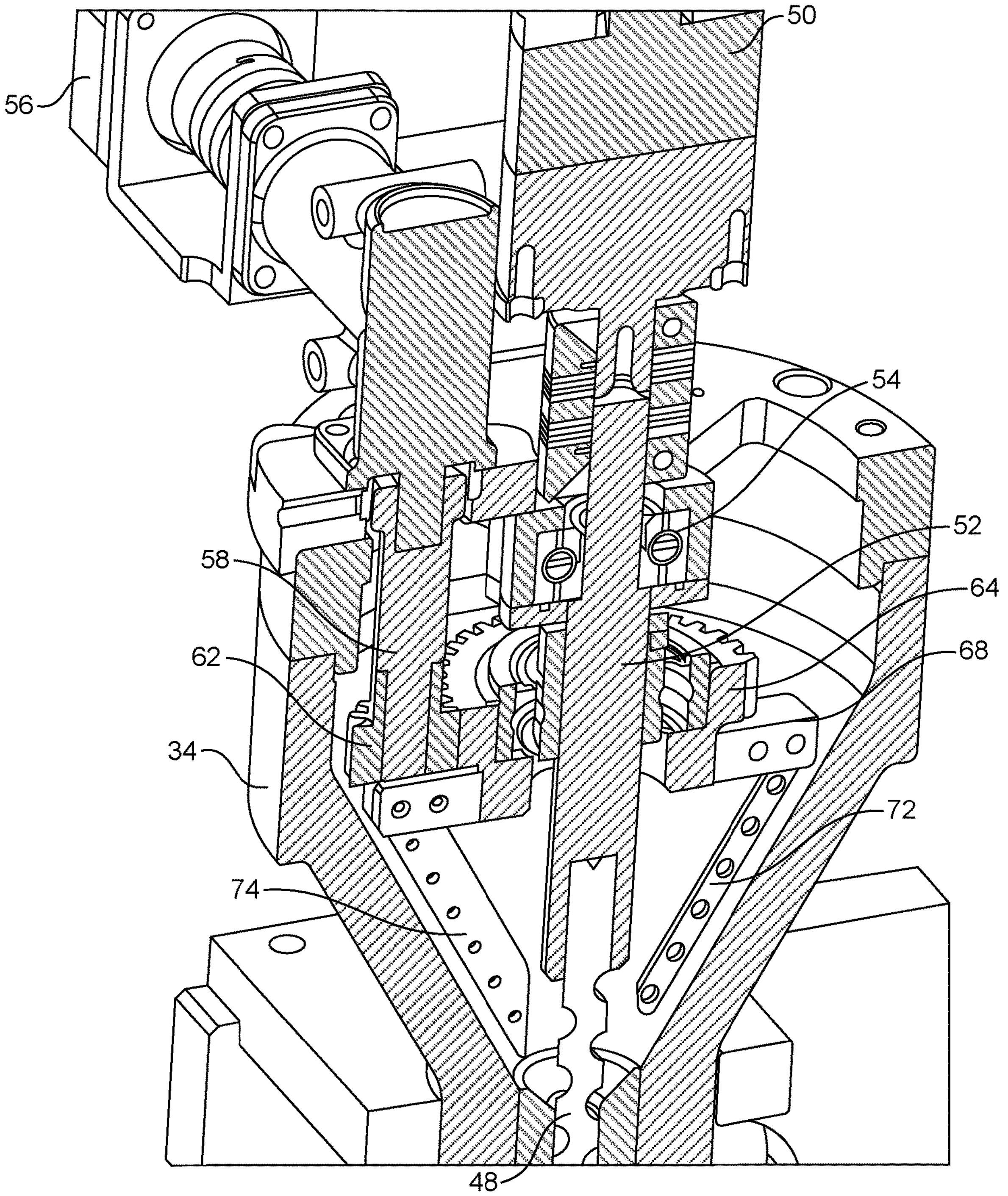
FIG. 9 is fragmentary cross section perspective of the housing assembly.

Referring to FIGS. 7-9, the mixing chamber 34 includes a first cylindrical section 42, a conical section 44 extending from the first cylindrical section, and a second cylindrical section 46 extending from the conical section. An auger screw 48 (broadly, a first mixer) extends axially through the mixing chamber 34 from the conical section 44 to the second cylindrical portion 46. The auger screw 48 is attached to a first motor 50 by a first drive shaft 52 for rotating the screw within the mixing chamber. Bearings 54 are disposed around the drive shaft 52 to facilitate rotation of the drive shaft and thus the auger screw 48 along the axis of the mixing chamber 34. A second motor 56 is mounted on the housing assembly 14 and is configured to rotate a second drive shaft 58 coupled to a gear assembly 60 disposed in the mixing chamber 34. In one embodiment, the motors 50, 56 are servo motors. However, other types of motors can be used without departing from the scope of the disclosure.

The gear assembly 60 includes a first gear 62 configured to rotate about the rotational axis of the second drive shaft 58 in the first direction, and a second gear 64 meshed with the first gear such that rotation of the first gear causes the second gear to rotate in a second direction opposite the first direction. The second gear 64 is positioned around and concentric with the first drive shaft 52 such that the second gear and auger screw 48 generally rotate about a common axis. A wiper assembly 66 (broadly, a second mixer) is attached to the second gear 64 so that the wiper assembly rotates with the second gear 64. The wiper assembly 66 comprises a carrier 68 and a pair of wipers 70 attached to the carrier. The wipers 70 include a wiper body 72 and a blade 74 extending from the wiper body. In one embodiment, the blades 74 are bolted on to the wiper bodies 72. However, the blades 74 can be attached to the wiper bodies 72 by any suitable means without departing from the scope of the disclosure. Further, the blades 74 may comprise rubber strips. However, the blades 74 could have other configurations without departing from the scope of the disclosure. The wiper assembly 66 is generally disposed in the conical section 44 of the mixing chamber 34. The wipers 70 of the wiper assembly 66 follow the interior profile of the conical section 44 such that the wipers are angled inward toward a central axis of the mixing chamber 34 as they extend from a top to a bottom of the wipers. Other configurations of the mixing chamber 34 and wiper assembly 66 are also envisioned.

The auger screw 48 is operatively attached to the first motor 50, and the wiper assembly 66 is operatively attached to the second motor 56. Thus, the auger screw 48 and the wiper assembly 66 are independently rotatable. Therefore, the auger screw 48 can be operated to rotate in a first direction and the wiper assembly 66 can be operated to rotate in a second direction. The second direction of rotation for the wiper assembly 66 can be the same or opposite direction as the first direction of rotation for the auger screw 48. This creates the possibility of counter-rotation within the mixing chamber 34 that functions to mix and loosen the pollen in the mixing chamber. Additionally, the auger screw 48 can be operated to rotate at a first speed, and the wiper assembly 66 can be operated to rotate at a second speed that is the same or different from the first speed. This allows the mixing components in the mixing chamber 34 to counter rotate at different speeds to facilitate mixing of the pollen based on the amount and consistency of the pollen within the mixing chamber. For instance, over time the quantity of pollen in the mixing chamber 34 may diminish. Being able to adjust the speed and direction of rotation of the mixing components provides for smooth pollen movement within the mixing chamber 34.

Pollen entering the mixing chamber 34 from the funnel 36 is first mixed within the conical section 44 of the mixing chamber by the wiper assembly 66 and auger screw 48. The wiper assembly 66 also helps to push the pollen downward in the mixing chamber 34. As explained above, the wiper assembly 66 and auger screw 48 may rotate in the same or opposite direction and at the same or different speeds. Rotating the wiper assembly 66 in the opposite direction of the auger screw 48 helps to adequately mix and stir the pollen as well as push the pollen downward within the conical section 44 of the mixing chamber 34. The pollen then drops down into the second cylindrical section 46 of the mixing chamber 34 where the pollen is further mixed and transported along the second cylindrical section by the auger screw 48. The speed at which the auger screw 48 is rotated may be adjusted throughout the application process. In one embodiment, the rotation rate of the auger screw 48 is based on the speed at which the applicator device 10 is moved along the plants PR. For instance, increasing the speed of travel for the applicator device 10 may cause the rotation rate of the auger screw 48 to increase so that more pollen is mixed and moved along the mixing chamber. Conversely, reducing the speed of travel for the applicator device 10 may cause the rotation rate of the auger screw 48 to decrease so that less pollen is mixed and moved along the mixing chamber. This allows the appropriate amount of pollen to be delivered to the plants PR.

Figure 10:
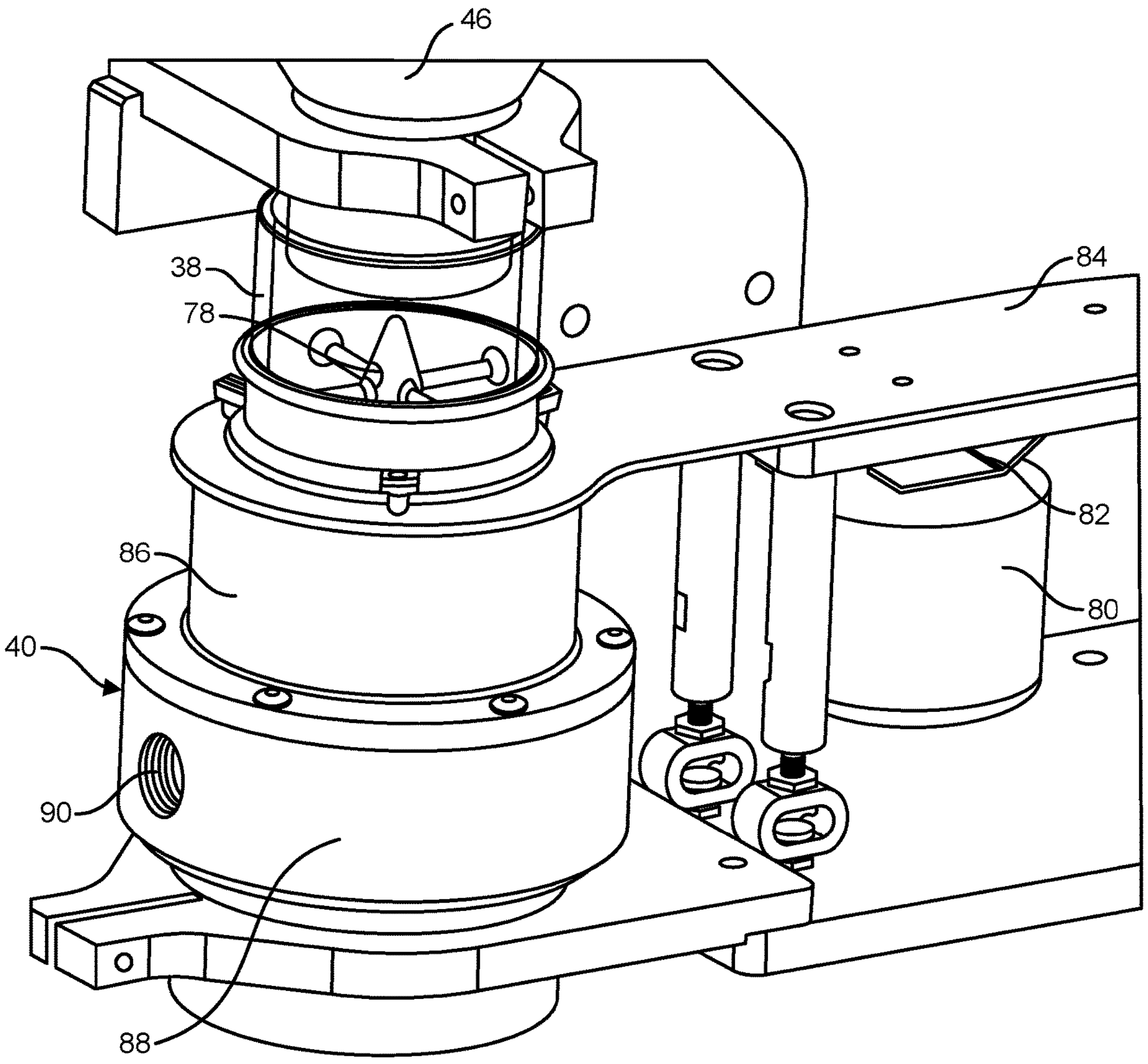
FIG. 10 is a fragmentary perspective of the housing assembly.

Referring to FIGS. 6 and 10, the mixed pollen in the mixing chamber 34 is then delivered to the sieve chamber 38. The sieve chamber 38 comprises a generally cylindrical housing. A sieve 78 is disposed in the sieve chamber 38. A vibrator 80 is operatively connected to the sieve chamber 38 for vibrating the sieve chamber. In the illustrated embodiment, a flange 82 attaches the vibrator 80 to a plate 84 disposed around the sieve chamber 38. Thus, vibration of the vibrator 80 is communicated to the sieve chamber 38 through the flange 82 and plate 84 for vibrating the sieve 78 and pollen in the sieve chamber. The vibrator 80 can be connected to the sieve chamber 38 by other means without departing from the scope of the disclosure. Vibration of the sieve 78 agitates the pollen causing the pollen to separate and fall through openings in the sieve to the bottom of the sieve chamber 38. This allows the mixed pollen to be even further separated for delivery to the applicator 16. An amplitude of vibration of the vibrator 80 may be electronically controlled. In one embodiment, a brush (not shown) is included in the sieve chamber 38 to help further break up any pollen clumps in the sieve chamber. The sieve chamber 38 may have other configurations without departing from the scope of the disclosure. Additionally, the sieve chamber 38 can be omitted from the housing assembly 14.

Pollen then falls from the bottom of the sieve chamber 38 and into the airflow chamber 40. The airflow chamber 40 comprises a transition section 86 attached to the bottom of the sieve chamber 38 and extending generally vertically, and an airflow section 88 at a bottom of the transition section that extends generally vertically from the transition section. Thus, pollen falls vertically through the transition section 86 and into the airflow section 88. The airflow section 88 is configured for fluid communication with a blower (not shown) mounted to the airflow chamber 40. In the illustrated embodiment, the airflow section 88 includes a threaded opening 90 for attaching a blower to the airflow chamber 40. The blower produces a flow of air through the airflow section 88 that is generally parallel to the longitudinal axis of the airflow section. Thus, activation of the blower produces an airstream that flows generally parallel to the direction in which the pollen falls through the airflow chamber 40 to expels the pollen from the airflow chamber and into the applicator 16. In one embodiment, the blower creates a flow velocity of at least 2.0 m/s. In a preferred embodiment, the blower creates a flow velocity of about 3.1 m/s. It is important the flow velocity does not interfere with adhesion of pollen with the silks. The blower may create other flow velocities. However, it has been found that the disclosed flow rates provide a low impact delivery process which maintains the viability and health of the pollen. Additionally, it will be understood that the airflow chamber 40 may be constructed in other ways without departing from the scope of the disclosure. For instance, the airflow section 88 may extend generally horizontally such that a blower attached to the airflow section will produce a flow of air that is generally perpendicular to the direction in which the pollen falls through the airflow chamber 40. Still other configurations are envisioned.

Figure 11:
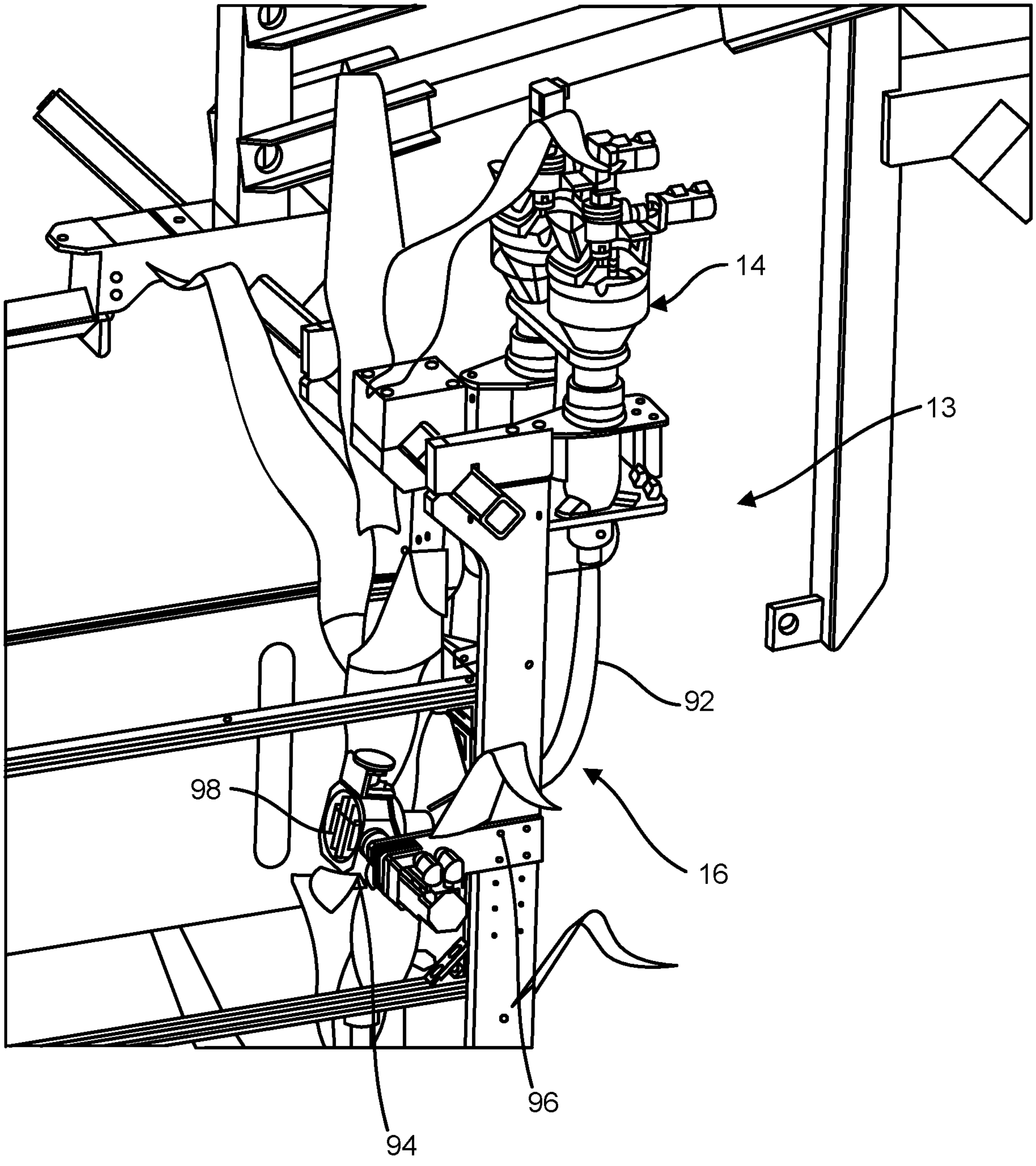
FIG. 11 is a fragmentary perspective of the pollen applicator device showing a pollen applicator assembly.
Figure 12:
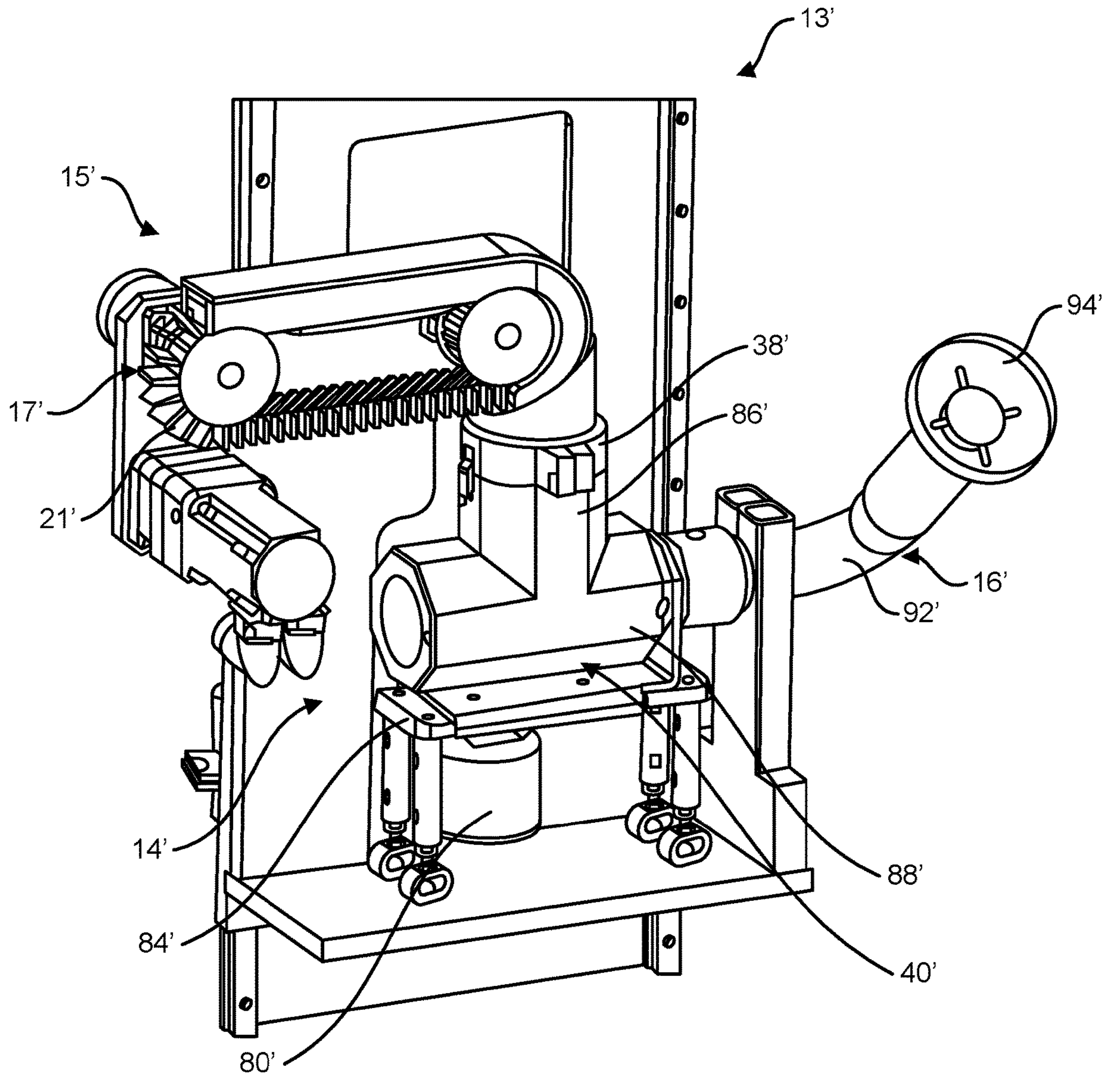
FIG. 12 is a perspective of a pollen applicator assembly of another embodiment.
Figure 13:
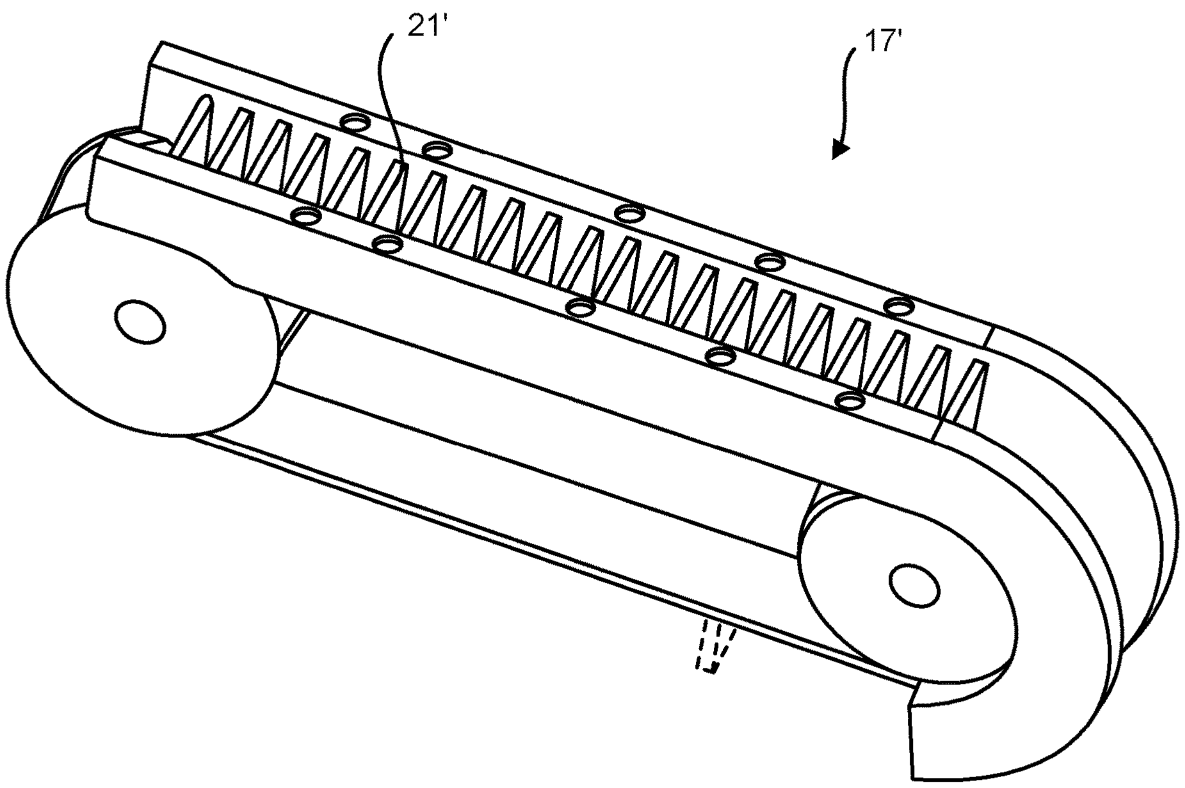
FIG. 13 is a perspective of a conveyor assembly of the applicator assembly of FIG. 12.
Figure 14A:
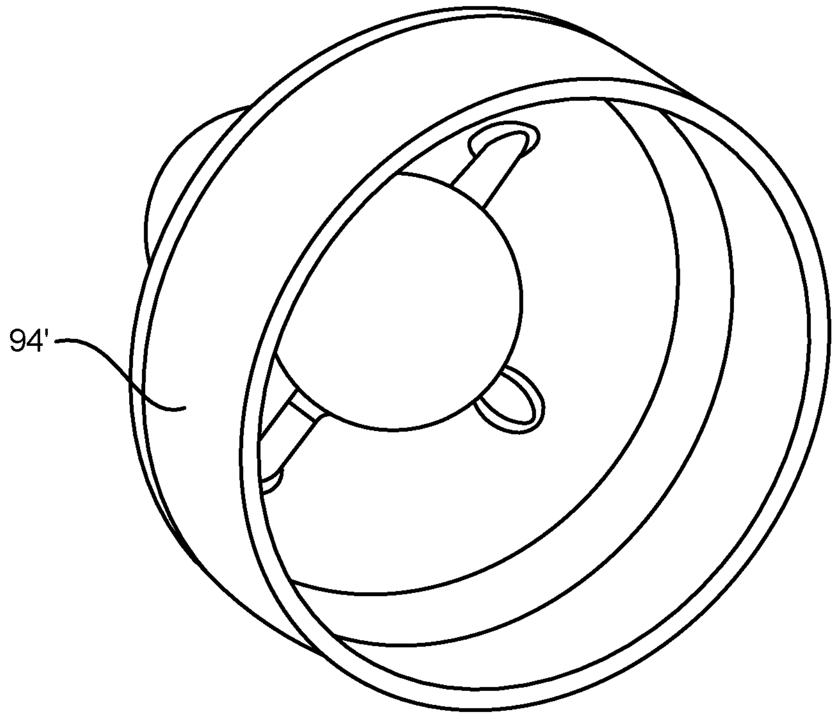
FIG. 14A is a perspective of a nozzle of the pollen applicator assembly of FIG. 12.
Figure 14B:
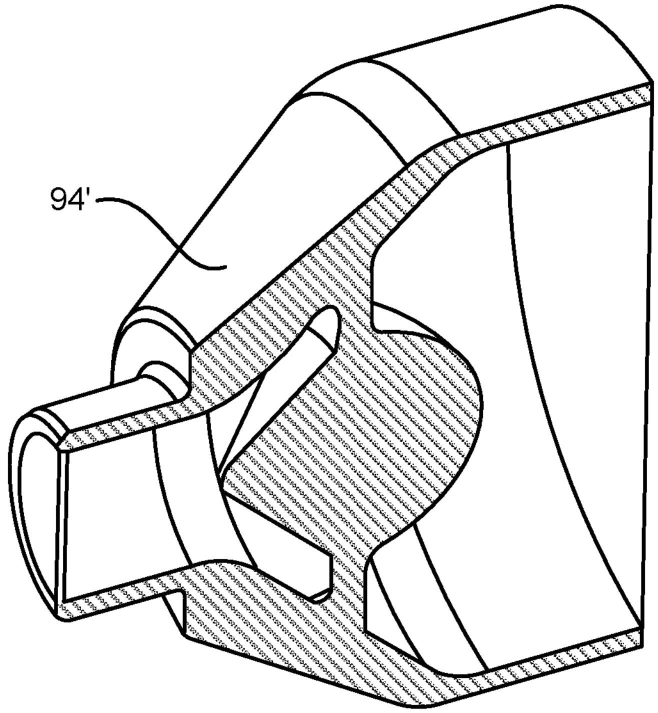
FIG. 14B is a cross section of the nozzle in FIG. 14A.

Referring to FIG. 11, the applicator 16 comprises a flexible hose 92 attached to an outlet of the airflow section 88 of the airflow chamber 40 at a first end of the hose, and a nozzle 94 attached to an opposite end of the hose for applying the pollen to the plants PR. In one embodiment, the flexible hose 92 is free of a coating or oil within an interior of the hose. The flexible nature of the hose 92 allows the nozzle 94 to be selectively positioned. For instance, the nozzle 94 may be oriented such that an outlet of the nozzle faces in a backwards direction with respect to the direction of travel of the applicator assembly 13. Additionally, the nozzle 94 may be angled inward toward the adjacent applicator assembly 13 so that the outlet is pointed generally in the direction of the plants PR. A height of the nozzle 94 above the ground may also be selectively positioned. In the illustrated embodiment a nozzle bracket 96 mounts the nozzle 94 to one of the lateral brackets 22L of the frame 18. The nozzle bracket 96 can be selectively positioned along the lateral bracket 22L. In one embodiment, the nozzle bracket 96 is positioned such that the nozzle 94 is located generally about 8 inches above the silks of the plants PR. In one embodiment, the nozzle 94 is located between about 5 and about 10 inches above the silks.

The nozzle 94 may also be operatively connected to an actuator (not shown) to automatically adjust the position of the nozzle. For instance, a sensor (not shown) may detect the position of the silks of the plants and signal the actuator to adjust the position/orientation of the nozzle for optimal application of the pollen to the plants. In this embodiment, a vertical and/or angular/rotational position of the nozzle 94 may be adjusted to optimize the delivery of pollen to the plants. In one embodiment, the nozzle 94 may be configured for 2-axis gimballing and gross vertical movement. The configuration of the applicator 16 ensures that a greater percentage of pollen will be applied to the plants PR. The nozzle 94 can be oriented in other positions and directions without departing from the scope of the disclosure. For example, the outlet of the nozzle 94 may face in the forward direction of travel with respect to the applicator assembly 13. Still other positions and orientations are envisioned. Further, the nozzle 94 may be constructed such that the nozzle produces a cloud of pollen when the pollen is expelled from the nozzle. In particular, the nozzle 94 may include a vent 98 disposed in the housing, and a ball (not shown) disposed in the housing adjacent the outlet of the nozzle. The vent 98 comprises a grate structure defined by a plurality of vertical blades. Pollen entering into the nozzle 94 passes around the ball and through the vent 98 whereby the pollen is formed into a cloud like formation. This specific cloud structure replicates the way in which pollen is introduced to the silks of plants in nature.

A suitable method of using the pollen applicator device 10 to apply pollen to crop plants will now be briefly described. The method described below is specifically directed toward the application of pollen to corn plants. However, the same techniques can be employed in applying pollen to other types of crops. As explained above, and with reference to FIG. 1, the illustrated pollen applicator devices 10 are spaced apart along the width of the base B of the tractor T to apply pollen to rows of pollen-receiving corn plants PR.

After the plants PR are grown such that they are suitable for pollination, an operator installs the pollen applicator devices 10 on the tractor T. The operator may, for example, measure or visually inspect the heights of the plants PR and adjust the height of the applicator assemblies 13 by moving the linkage 19 so that the shields 28 are positioned for receiving the plants PR within an interior space defined by the shields. Additionally or alternatively, the operator may position the nozzles 94 mounted on the lateral brackets 22L such that the nozzles are disposed at a predetermined height above the silks of the plants PR (e.g., about 8 inches) so that the pollen being expelled from the nozzles is at a preferred height for being applied to the plants. The heights of the pollen applicator assemblies 13 and/or nozzles 94 may also be automatically adjusted through use of the sensors, controllers, and the actuators (e.g., hydraulic pistons) mounted on the tractor T.

In use, the tractor T can be driven through a field of corn plants PR along a row of plants. The operator initially loads the applicator assemblies 13 with pollen through the funnels 36 of the housing assemblies 14. The motors 50, 56 are activated to rotate the auger screws 48 and wiper assemblies 66 to mix the pollen within the mixing chambers 34. The mixed pollen is then transferred by the auger screw 48 to the sieve chambers 38 where the mixed pollen is agitated by the vibrating sieve chambers causing the pollen to be further separated. The further separated pollen is sifted through the sieves 78 and into the airflow chambers 40 where the blowers push the pollen to the applicators 16. The applicators 16 spray the pollen onto the plants PR as the applicator assemblies 13 are moved past the plants. Further, as a pollen applicator device 10 moves through a row of plants PR, the shields 28 contain the pollen sprayed from the nozzles 94 to within the row of plants to maximize the amount of pollen that reaches the plants. Therefore, the pollen applicator device 10 can effectively apply pollen to the plants PR using pollen that has been collected and stored such that the pollen may have become clumped and/or hardened, or pollen that has been mixed with additives changing the consistency of the pollen. The applicator device 10 processes the stored pollen prior to being applied to the plants PR making the pollen suitable for pollination.

In one embodiment, the presence of certain additives can minimize the efficiency of pollen application by competing for adhesion sites on the recipient stigma, preventing proper pollen adhesion to the recipient stigma, or by damaging the recipient stigma. Consequently, it may not be desirable to apply additives towards the recipient stigma. To address this concern, additives may be separated from the pollen by using differences in size and/or density. Non-limiting examples of separation systems that may be employed include air classifiers, sieves, air jet sieves, gravity settling chambers, and tuned cyclonic separators. Once separated from the pollen, the additive can be collected for potential reuse or dispensed away from the stigmas.

Referring to FIGS. 12-14B, an applicator assembly of another embodiment is generally indicated at 13'. The applicator assembly 13' can be used for small plot testing. The applicator assembly 13' comprises a conveyor assembly 15' configured to receive pollen previously collected from pollen bearing plants, a housing assembly 14' attached to the conveyor assembly for receiving metered amounts of pollen from the conveyor assembly, and an applicator 16' connected to the housing assembly for applying the pollen to the plants.

The conveyor assembly 15' comprises a slated timing belt 17' and a motor operatively connected to the timing belt for turning the belt. The speed at which the motor turns the timing belt 17' may be adjusted based on the speed the applicator assembly 13' moves along the plants. The timing belt 17' meters predetermined amounts of pollen between slats 21' on the timing belt. The timing belt 17' carries the metered amounts of pollen to the housing assembly 14'. It will be understood that the convey assembly 15' can have other configurations without departing from the scope of the disclosure.

The housing assembly 14' comprises a sieve chamber 38' in communication with an outlet of the timing belt 17' for receiving the metered pollen and separating and dispersing the pollen, and an air flow chamber 40' attached to the bottom of the sieve chamber for directing the separated pollen out of the housing assembly. The housing assembly 14' is configured to sufficiently mix and separate the pollen such that collected pollen which may have clumped together over a period of time is able to be loosened and broken up. Therefore, pollen that is sent to the applicator 16' for being applied to the plants is in a suitable condition for fertilizing the plants. It will be understood that the housing assembly 14' may have other configurations without departing from the scope of the disclosure.

The sieve chamber 38' comprises a generally cylindrical housing. A sieve (not shown) is disposed in the sieve chamber 38'. A vibrator 80' is operatively connected to the sieve chamber 38' for vibrating the sieve chamber. In the illustrated embodiment, the vibrator 80' is attached to a plate 84' under the housing assembly 14'. Thus, vibration of the vibrator 80' is communicated to the sieve chamber 38' through the plate 84' for vibrating the sieve and pollen in the sieve chamber. The vibrator 80' can be connected to the sieve chamber 38' by other means without departing from the scope of the disclosure. Vibration of the sieve agitates the pollen causing the pollen to fall through openings in the sieve to the bottom of the sieve chamber 38'. The vibrator 80' may be set to vibrate at a specific amplitude for optimal pollen dispersion.

Pollen then falls from the bottom of the sieve chamber 38' and into the airflow chamber 40'. The airflow chamber 40' comprises a transition section 86' attached to the bottom of the sieve chamber 38' and extending generally vertically, and an airflow section 88' at a bottom of the transition section that extends generally horizontally from the transition section. Pollen falls vertically through the transition section 86' and into the airflow section 88'. The airflow section 88' is in fluid communication with a blower (not shown) that produces a flow of air through the airflow section to expel the pollen from the airflow chamber 40' to the applicator 16'. The flow of air is generally parallel to the longitudinal axis of the airflow section 88' and thus generally perpendicular to the direction in which the pollen falls through the airflow chamber 40'. It will be understood that the airflow chamber 40' may be constructed in other ways without departing from the scope of the disclosure.

The applicator 16' comprises a flexible hose 92' attached to an outlet of the airflow section 88' of the airflow chamber 40' at a first end of the hose, and a nozzle 94' attached to an opposite end of the hose for applying the pollen to the plants. The flexible nature of the hose 92' allows the nozzle 94' to be selectively positioned.

Referring to FIGS. 15-21, a pollen applicator device of another embodiment is generally indicated at 10". The pollen applicator device comprises a mounting assembly 12" configured to attach the applicator device to a support (i.e., tractor T) and a pollen dosing assembly 13" supported by the mounting assembly for applying the pollen to the plants PR. The pollen dosing assembly 13" includes a housing assembly 14" secured to the mounting assembly 12" and configured to receive pollen previously collected from pollen bearing plants, and a pollen distribution assembly 16" (FIG. 15) connected to the housing assembly for receiving the pollen from the housing assembly and applying the pollen to pollen receiving plants PR in a field.

Figure 16:
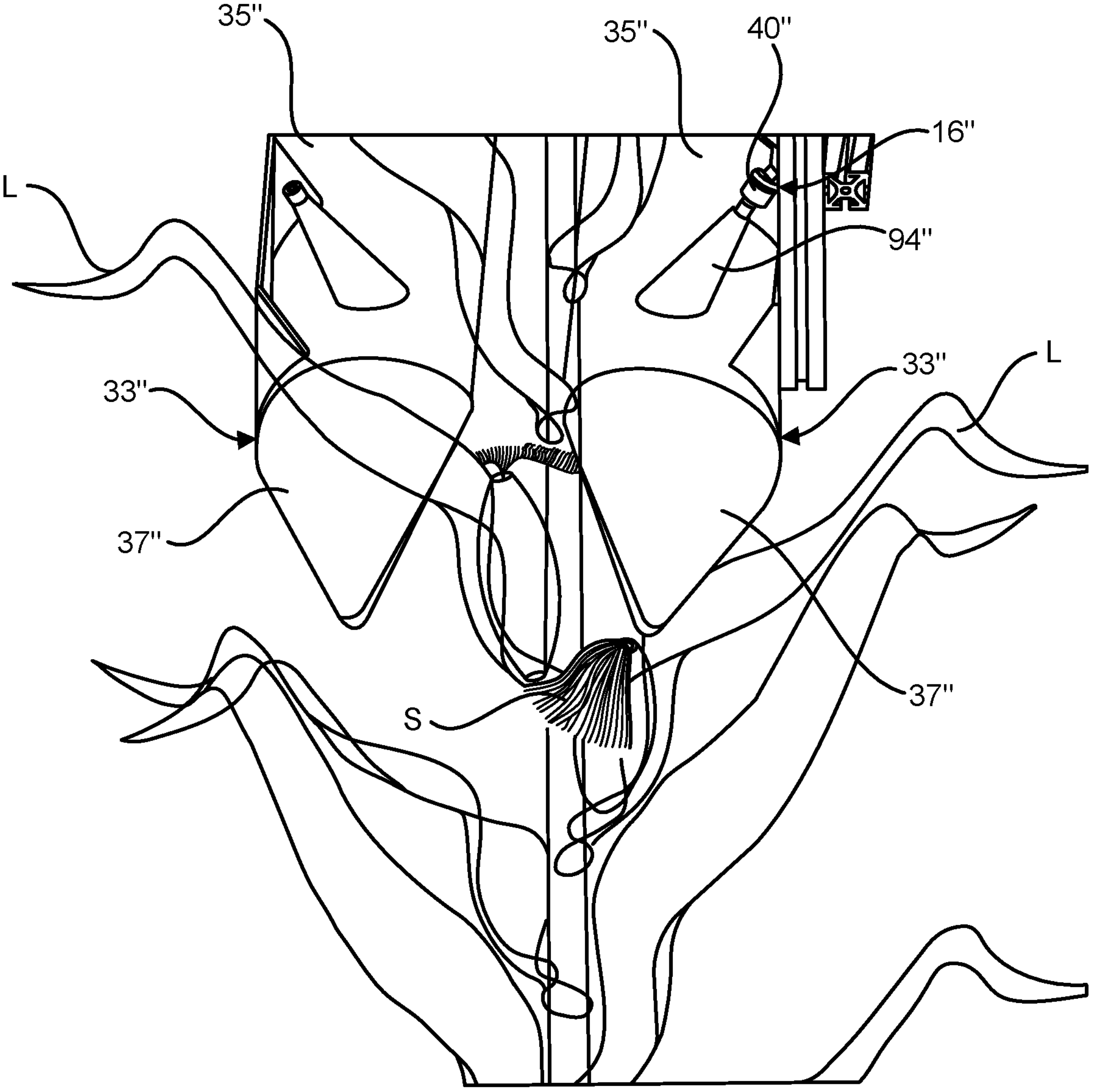
FIG. 16 is an enlarged fragmentary perspective of the pollen applicator device of FIG. 15.

Guide assemblies 30" are attached to the mounting assembly 12" and extend forwardly on the mounting assembly. The guide assemblies 30" each include a mount 31" attached to the mounting assembly 12" for mounting the guide assembly to the mounting assembly, and a separator 33" attached to the mount 31" and extending forwardly from the mount. The separator 33" is configured to separate the leaves L from the silks S as the pollen dosing assembly 13" is moved along the plants (FIG. 16). In the illustrated embodiment, the separators 33" include a semi-cylindrical base 35" and a semi-conical projection 37" extending forwardly from the base. Interior sides of the semi-conical projections 37" form a funnel for guiding the silks S between the guide assemblies 30" for applying the pollen to the silks, and exterior sides of the semi-conical projections function as diverters for diverting the leaves L away from the pollen application area between the separators 33". Thus, the guide assemblies 30" maximize the amount of pollen that is applied to the silks S of the plants PR by keeping the leaves L from blocking the pollen that would otherwise be applied to the silks. The guide assemblies 30" may have other configurations or may be omitted without departing from the scope of the disclosure.

Figure 18:
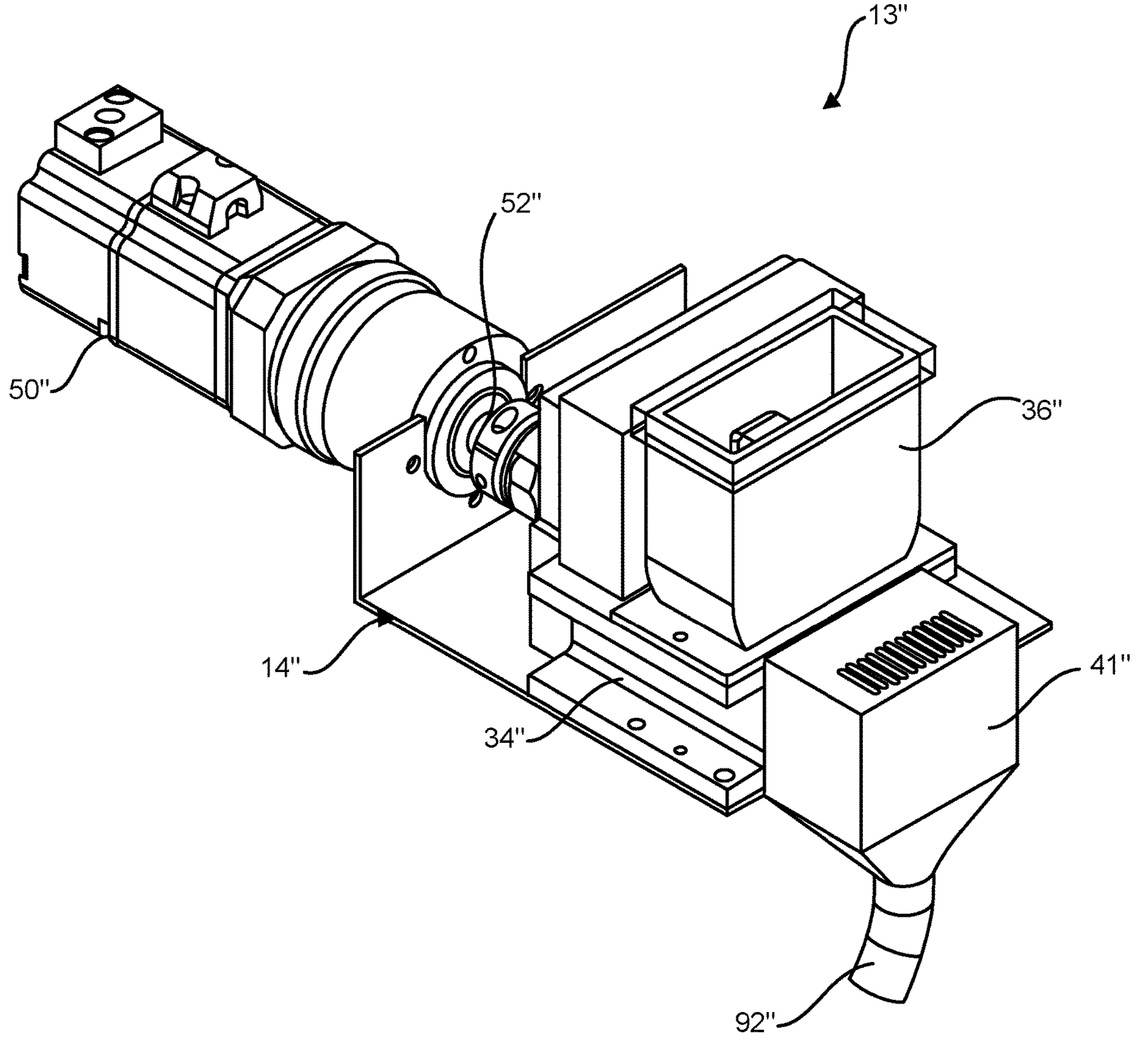
FIG. 18 is a perspective of a pollen dosing assembly of the pollen applicator device in FIG. 15.
Figure 19:
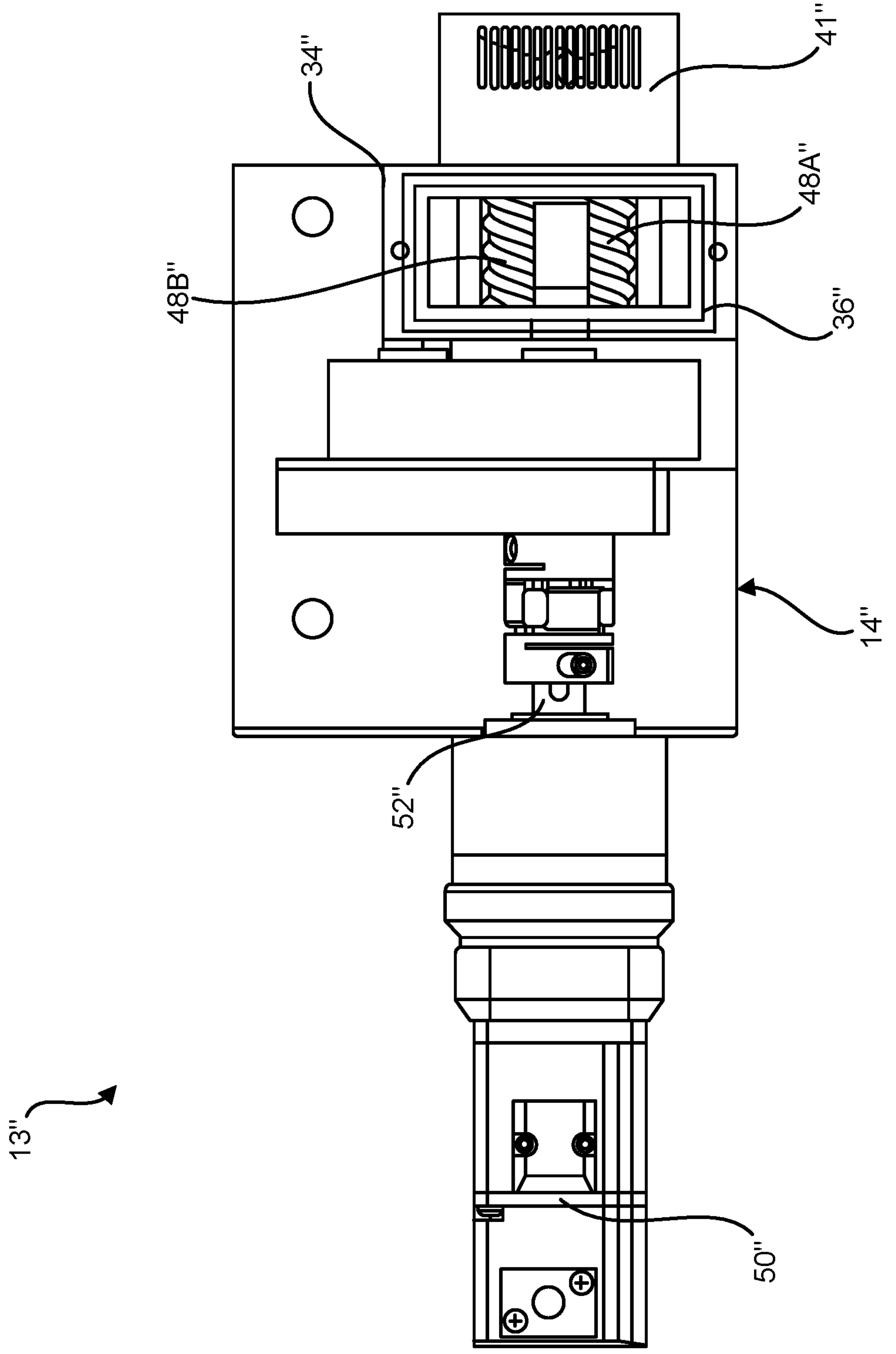
FIG. 19 is a top view of the pollen dosing assembly in FIG. 18.

Referring to FIGS. 18 and 19, the housing assembly 14" comprises a feeding chamber 34" for mixing the pollen in the housing assembly, a funnel 36" attached to a top of the feeding chamber for funneling the collected pollen into the feeding chamber, and an outlet chamber 41" attached to an end of the feeding chamber for receiving the mixed pollen from the feeding chamber. The pollen distribution assembly 16" (FIG. 15) is in communication with the outlet chamber 41" for further separating and dispersing the mixed pollen, and directing the mixed and separated pollen out of the housing assembly 14" to the plants. It will be understood that the housing assembly 14" may have other configurations without departing from the scope of the disclosure.

Prior to delivering the pollen to the feeding chamber 34", the pollen may be stored in a temperature controlled container (not shown). For example, the pollen could be stored in a thermos, insulated housing, a refrigeration system, or the like, to keep the pollen cool before it is delivered to the feeding chamber 34". In one embodiment, the temperature controlled container is configured to maintain the pollen at near cryogenic conditions. In one embodiment, the temperature controlled container is configured to maintain the pollen at a temperature of between about 0 to about 10 degrees C. In one embodiment, the temperature controlled container is configured to maintain the pollen in the same condition the pollen was in for short-term storage prior to being delivered to the pollen dosing assembly 13". The stored pollen may be in a granular form. Alternatively, the applicator device 10" could be configured for use with stored pollen in a liquid solution.

Figure 20:
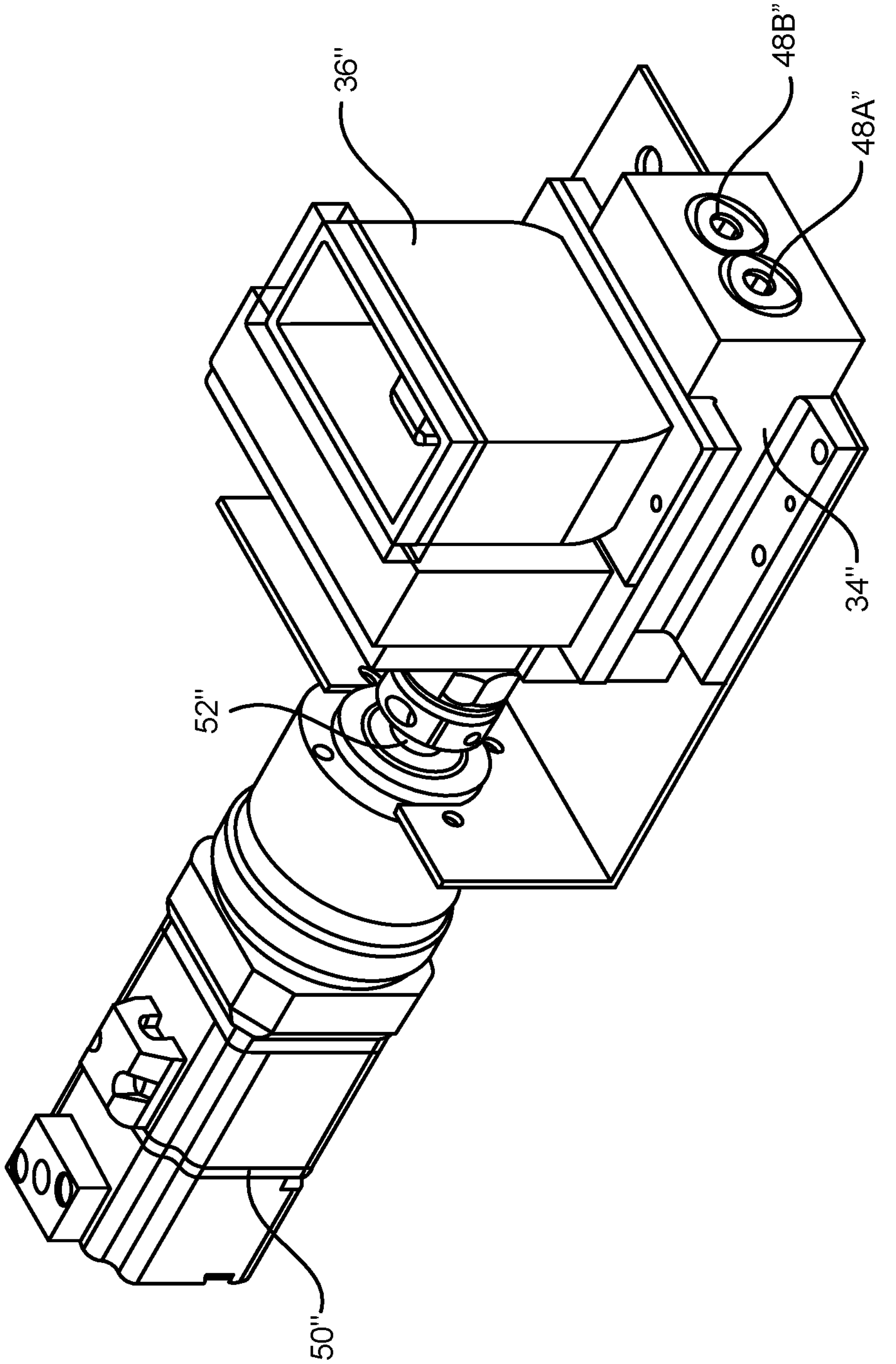
FIG. 20 is a perspective of the pollen dosing assembly in FIG. 18 with an outlet chamber removed.
Figure 21:
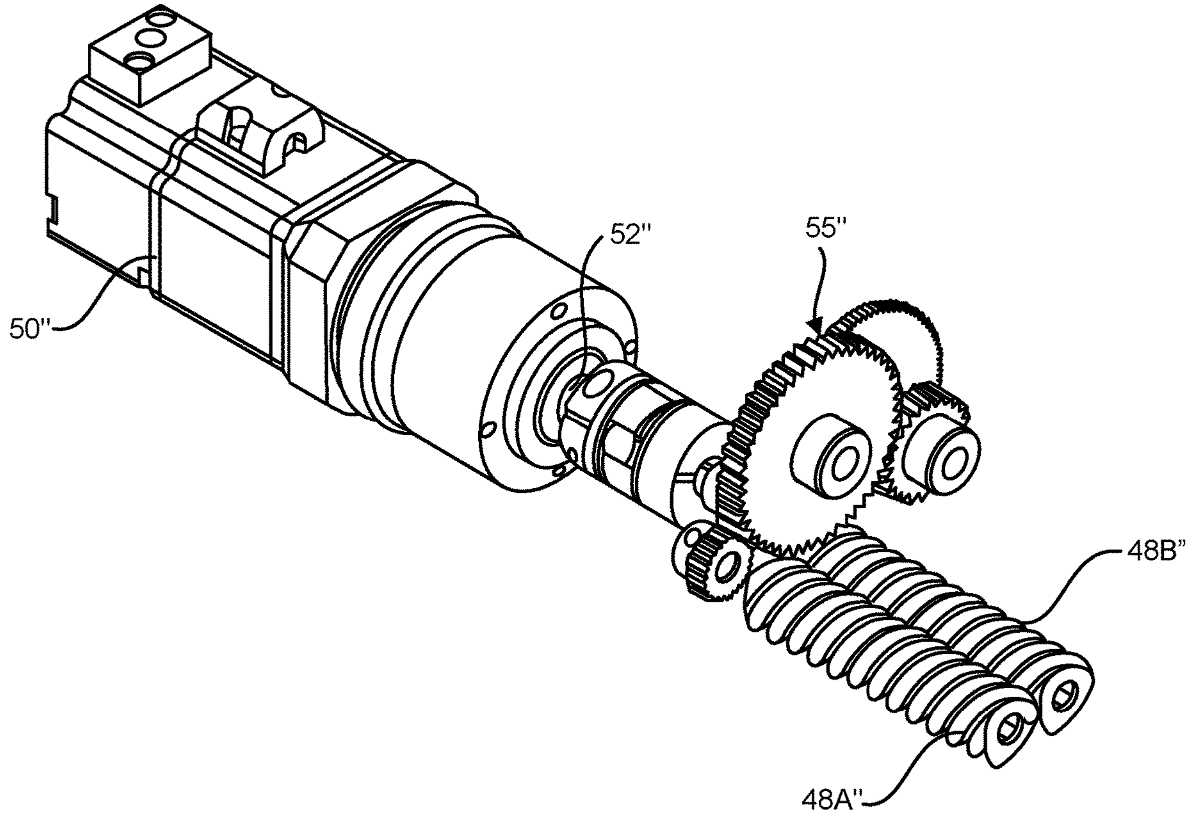
FIG. 21 is a perspective of the pollen dosing assembly in FIG. 18 with portions removed showing internal detail.

Referring to FIGS. 19-21, the feeding chamber 34" comprises a horizontal feeding chamber such that the pollen is advanced generally horizontally through the feeding chamber. The feeding chamber 34" includes a single mixing section extending horizontally through the feeding chamber. A pair of auger screws 48A", 48B" (broadly, first and second mixers) extend axially through the single mixing section of the feeding chamber 34". The auger screws 48A", 48B" are operatively connected to a motor 50" by a drive shaft 52" and gear assembly 55" for rotating the screws within the feeding chamber. In one embodiment, the motor 50" is a servo motor. However, other types of motors can be used without departing from the scope of the disclosure. Additionally, each auger screw 48A", 48B" can be operatively connected to a dedicated motor for rotating the auger screws. As such, the gear assembly 55" could be omitted without departing from the scope of the disclosure. Alternatively, a mixing and conveying mechanism other than auger screws can be used. In one embodiment, a rotary pill press (not shown) is used to deliver doses of pollen to the distribution assembly 16".

Activation of the motor 50" causes the gears of the gear assembly 55" to rotate. The engagement of the gears of the gear assembly 55" with the auger screws 48A", 48B" causes the screws to rotate. In one embodiment, the first auger screw 48A" is operable to rotate in a first direction and the second auger screw 48B" is operable to rotate in a second direction. The second direction of rotation for the second auger screw 48B" can be the same or opposite direction as the first direction of rotation for the first auger screw 48A". This creates the possibility of either co-rotation or counter-rotation within the feeding chamber 34" that functions to mix and loosen the pollen in the feeding chamber as the auger screws 48A", 48B" axially transport the pollen through the feeding chamber. Additionally, the dual auger configuration provides a self-cleaning function for the feeding chamber 34" by having the threads of one auger screw 48A", 48B" wipe away the pollen from the threads of the other auger screw.

The speed at which the auger screws 48A", 48B" are rotated may be adjusted throughout the application process. In one embodiment, the rotation rate of the auger screws 48A", 48B" is based on the speed at which the applicator device 10" is moved along the plants PR. For instance, increasing the speed of travel for the applicator device 10" may cause the rotation rate of the auger screws 48A", 48B" to increase so that more pollen is mixed and moved along the feeding chamber. Conversely, reducing the speed of travel for the applicator device 10" may cause the rotation rate of the auger screws 48A", 48B" to decrease so that less pollen is mixed and moved along the feeding chamber. This allows the appropriate amount of pollen to be delivered to the plants PR.

Referring to FIGS. 16-19, the mixed pollen in the feeding chamber 34" is then delivered to the outlet chamber 41" where the mixed pollen is funneled to the pollen distribution assembly 16" through hose 92". The pollen distribution assembly 16" comprises an airflow generator 40" and a nozzle 94" attached to an outlet of the airflow generator. The nozzle 94" directs the mixed pollen to the plants PR. An air current in the airflow generator 40" agitates the pollen causing the pollen to separate as they travel through the airflow generator and nozzle 94". This allows the mixed pollen to be even further separated for delivery by the pollen distribution assembly 16". The airflow generator 40" may be a cylindrical chamber having an internal diameter of about ⅜ inch. It will be understood that the airflow generator 40" may be constructed in other ways without departing from the scope of the disclosure. Additionally, adjusting the airflow through the airflow generator 40" can control the intensity of deglomeration of the pollen. In one embodiment, the airflow generator 40" creates a flow velocity of at least 2.0 m/s. In a preferred embodiment, the airflow generator 40" creates a flow velocity of about 3.1 m/s. In one embodiment, the airflow generator 40" is an eductor. Additionally, valves may be provided to quickly turn on and off airflow out of the nozzle 94".

Figure 15:
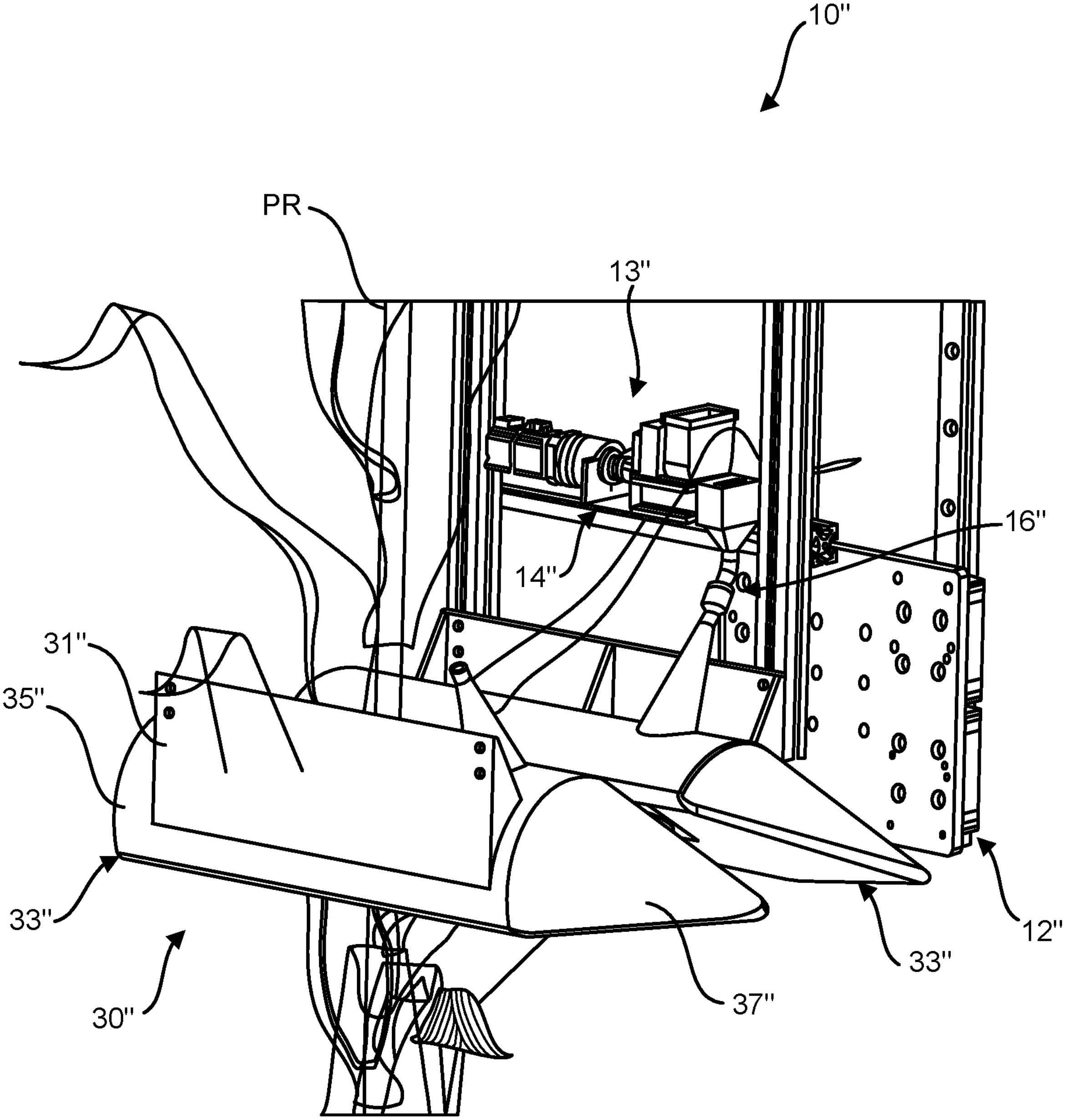
FIG. 15 is a fragmentary perspective of a pollen applicator device of another embodiment.
Figure 17:
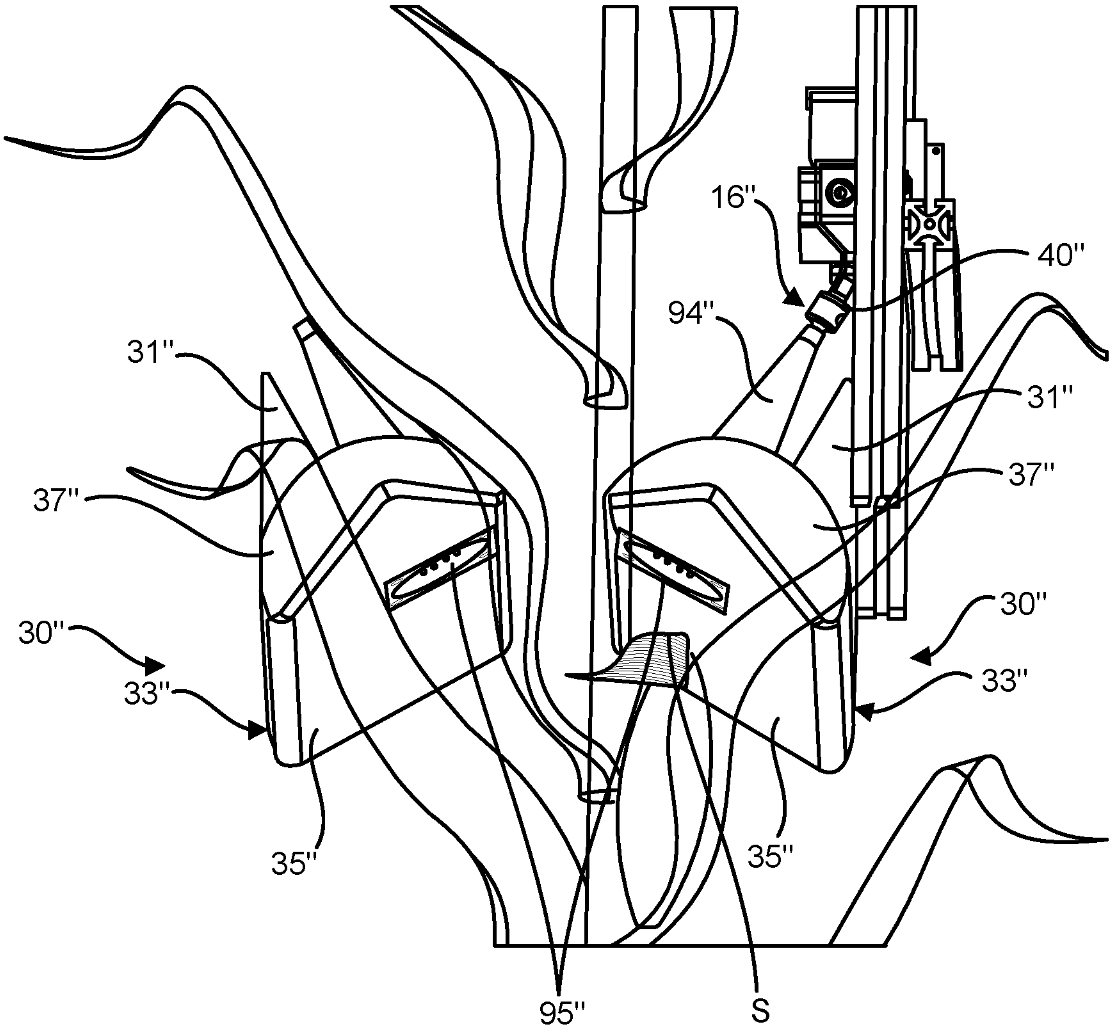
FIG. 17 is another fragmentary perspective of the pollen applicator device in FIG. 15.

Referring to FIG. 15-17, the nozzle 94" extends through a respective separator 33 of a guide assembly 30" such that an outlet 95" (FIG. 17) of the nozzle opens at a bottom surface of the semi-cylindrical base 35" of the separator. Therefore, the pollen expelled from the pollen distribution assembly 16" has a direct path to the silks S funneled between the separators 33" so that the maximum amount of pollen is applied to the silks. In one embodiment, the nozzle 94" tapers outward from an inlet to the outlet 95" of the nozzle. This shape can provide for a better dispersal of the pollen in a cloud and can decelerate the pollen flow coming from pollen distribution assembly 16" to simulate the way in which pollen is dispersed in nature. The nozzle 94" may also be operatively connected to an actuator (not shown) to automatically adjust the position of the nozzle. In one embodiment, a sensor, such as an optical sensor, (not shown) may detect the position of the silks of the plants and signal the actuator to adjust the position/orientation of the nozzle for optimal application of the pollen to the plants. In this embodiment, a vertical and/or angular/rotational position of the nozzle 94" may be adjusted to optimize the delivery of pollen to the plants. In one embodiment, the nozzle 94" may be configured for 2-axis gimballing and gross vertical movement. The gross vertical movement is configured to locate the nozzle 94" in the approximate location of the target silk. The 2-axis gimbal is configured to aim the nozzle directly at the target silk. After applying the pollen to the target silk, the nozzle 94" may be programmed to slew forward to start targeting the next silk in the row. Accordingly, this configuration of the pollen distribution assembly 16" ensures that a greater percentage of pollen will be applied to the plants PR.

Additionally or alternatively, the silks of the plants can be sensed directly using machine vision techniques. In this embodiment, a silk is recognized in an image and the location of the silk is recorded in the device 10" to instruct the distribution assembly 16" where to direct the pollen.

Additionally or alternatively, a dose rate of the device 10" can be varied during use to match the location of the plants, and in particular silks, along the row. In one embodiment, the device 10" may be operated with a sinusoidal dosing rate pattern. The sinusoidal dosing is configured to match the position of the silks on the plants and the spacing of the individual plants in the row. Other dosing rates/patterns may also be used.

Additionally or alternatively, the airflow generator 40" may connect to multiple hoses or passages for providing multiple pollen flow outlets to direct pollen toward plants in multiple rows. As such, each hose may have a nozzle or other suitable outlet for dispersing the pollen in the desired manner. Similarly, the hose 92" may communicate with multiple nozzles 94" attached to the mounting assembly 12". The device 10" may activate one of the nozzles 94", such as by reference to a location of the silks by a sensor, and deactivate the other nozzles so that all or substantially all of the pollen is delivered in the direction of the silks. This embodiment has the advantage of being able to incorporate a single larger dosing unit and nozzles attached to the dosing unit for delivering pollen at each row. Accordingly, there is only one place to refill the applicator with pollen, which reduces the downtime and labor required to add pollen to the equipment. By having the pollen stored in one location, it makes it more feasible to have environmental (e.g., temperature and humidity) controls to maintain pollen quality during the application process. This will allow for longer runs between having to refill the applicator with pollen, therefore increasing the number of acres that can be applied in a given time period.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A pollen applicator device for a tractor, for applying pollen to crop plants grown in rows as the tractor moves through the rows of crop plants, the device comprising:

a mounting assembly attachable to a base of the tractor, so that the tractor can transport the pollen applicator device, via the mounting assembly, through a row of crop plants;

a housing assembly coupled to the mounting assembly, the housing assembly comprising:

an inlet for receiving pollen into the housing assembly; and a first mixer mounted within the housing assembly, the first mixer operable to mix the received pollen within the housing assembly as the pollen applicator device is transported by the tractor through the row of crop plants;

an applicator in fluid communication with the housing assembly and operable to receive the mixed pollen from the housing assembly;

wherein the applicator includes a nozzle attached to the mounting assembly, the nozzle configured to discharge the received pollen at the crop plants as the tractor transports the pollen applicator device through the row of crop plants; and at least one guide attached to the mounting assembly apart from the nozzle, the at least one guide configured to direct silks of the plants through the at least one guide and into an airflow path of the applicator for applying pollen to the silks of the plants directed through the at least one guide.

2. The pollen applicator device as set forth in claim 1, wherein the first mixer is mounted within a mixing chamber of the housing assembly.

3. The pollen applicator device as set forth in claim 2, wherein the first mixer is configured to rotate within the mixing chamber to mix the pollen received in the housing assembly.

4. The pollen applicator device as set forth in claim 3, wherein the housing assembly includes a second mixer mounted within the mixing chamber, and wherein the second mixer is configured to rotate within the mixing chamber independently from the first mixer to further mix the pollen received in the housing assembly.

5. The pollen applicator device as set forth in claim 4, wherein the first mixer comprises a first auger screw and the second mixer comprises a second auger screw.

6. The pollen applicator device as set forth in claim 2, wherein the housing assembly further includes an airflow chamber disposed below the mixing chamber, the air flow chamber in communication with the mixing chamber such that the pollen mixed in the mixing chamber is delivered to the airflow chamber, the airflow chamber configured to produce an airflow for delivering the pollen from the airflow chamber to the applicator.

7. The pollen applicator device as set forth in claim 6, wherein a position of the nozzle of the applicator is automatically adjustable relative to the mounting assembly as the tractor transports the pollen applicator device through the row of crop plants, to optimize delivery of the pollen to the crop plants.

8. A system for applying pollen to crop plants grown in rows, the system comprising:

a tractor having a base; and the pollen applicator device as set forth in claim 1;

wherein the mounting assembly is movably attachable to the base of the tractor to adjust a position of the housing assembly on the base.

9. The pollen applicator device as set forth in claim 1, wherein the at least one guide is further configured to divert leaves of the plants away from the applicator.

* * * * *